US007460637B2

(12) United States Patent
Clinthorne et al.

(10) Patent No.: US 7,460,637 B2
(45) Date of Patent: *Dec. 2, 2008

(54) HIGH SPATIAL RESOLUTION X-RAY COMPUTED TOMOGRAPHY (CT) METHOD AND SYSTEM

(75) Inventors: Neal H. Clinthorne, Ann Arbor, MI (US); Predrag Sukovic, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/259,870

(22) Filed: Oct. 27, 2005

(65) Prior Publication Data

US 2006/0067464 A1 Mar. 30, 2006

Related U.S. Application Data

(63) Continuation of application No. 10/183,146, filed on Jun. 25, 2002, now Pat. No. 7,099,428.

(51) Int. Cl.
*G01N 23/00* (2006.01)
(52) U.S. Cl. .......................................... 378/17; 378/20
(58) Field of Classification Search .................. 378/57, 378/195, 4–20
See application file for complete search history.

(56) References Cited

U.S. PATENT DOCUMENTS 4,549,307 A * 10/1985 Macovski .................. 378/145

4,590,558 A  5/1986 Glover et al.
4,709,333 A  11/1987 Crawford (Continued)

FOREIGN PATENT DOCUMENTS

EP   0 660 599 A1   6/1995

(Continued)

OTHER PUBLICATIONS

Clinthorne, Neal H., et al., A Simple Algorithm For Restoring Images From Pixellated Radiation Detectors, Conference Record 1998 IEEE Nuclear Science Symposium, pp. 1-8.

(Continued)

*Primary Examiner*—Hoon Song
(74) *Attorney, Agent, or Firm*—Brooks Kushman P.C.

(57) ABSTRACT

A high spatial resolution X-ray computed tomography (CT) system is provided. The system includes a support structure including a gantry mounted to rotate about a vertical axis of rotation. The system further includes a first assembly including an X-ray source mounted on the gantry to rotate therewith for generating a cone X-ray beam and a second assembly including a planar X-ray detector mounted on the gantry to rotate therewith. The detector is spaced from the source on the gantry for enabling a human or other animal body part to be interposed therebetween so as to be scanned by the X-ray beam to obtain a complete CT scan and generating output data representative thereof. The output data is a two-dimensional electronic representation of an area of the detector on which an X-ray beam impinges. A data processor processes the output data to obtain an image of the body part.

42 Claims, 10 Drawing Sheets

U.S. PATENT DOCUMENTS

| | | | |
|---|---|---|---|
| 4,812,983 | A | 3/1989 | Gullberg et al. |
| 5,042,487 | A | 8/1991 | Marquardt |
| 5,243,664 | A | 9/1993 | Tuy |
| 5,293,312 | A | 3/1994 | Waggener |
| 5,390,112 | A | 2/1995 | Tam |
| 5,400,379 | A | 3/1995 | Pfoh et al. |
| 5,461,650 | A | 10/1995 | Tam |
| 5,473,655 | A * | 12/1995 | Hu ................. 378/4 |
| 5,533,088 | A | 7/1996 | Fivez |
| 5,615,279 | A | 3/1997 | Yoshioka et al. |
| 5,644,612 | A | 7/1997 | Moorman et al. |
| 5,648,997 | A * | 7/1997 | Chao .............. 378/98.4 |
| 5,751,785 | A | 5/1998 | Moorman et al. |
| 5,778,045 | A | 7/1998 | Stetten et al. |
| 5,793,838 | A | 8/1998 | Kovacs |
| 5,798,924 | A | 8/1998 | Eufinger et al. |
| 5,805,659 | A | 9/1998 | Tam |
| 5,815,546 | A | 9/1998 | Flohr et al. |
| 5,864,146 | A | 1/1999 | Karellas |
| 5,878,108 | A | 3/1999 | Baa et al. |
| 5,881,123 | A | 3/1999 | Tam |
| 5,903,008 | A | 5/1999 | Li |
| 5,909,476 | A | 6/1999 | Cheng et al. |
| 5,921,927 | A * | 7/1999 | McArdle ............. 600/425 |
| 5,927,982 | A | 7/1999 | Kruger |
| 5,949,846 | A | 9/1999 | Stein et al. |
| 5,970,112 | A | 10/1999 | Hsieh |
| 5,995,580 | A | 11/1999 | Schaller |
| 5,999,587 | A | 12/1999 | Ning et al. |
| 6,018,563 | A | 1/2000 | Arai et al. |
| 6,035,012 | A | 3/2000 | Hsieh |
| 6,052,428 | A | 4/2000 | Nakano et al. |
| 6,075,836 | A | 6/2000 | Ning |
| 6,094,467 | A | 7/2000 | Gayer et al. |
| 6,101,234 | A | 8/2000 | Ali et al. |
| 6,101,236 | A | 8/2000 | Wang et al. |
| 6,104,775 | A | 8/2000 | Tuy |
| 6,118,841 | A | 9/2000 | Lai |
| 6,118,842 | A | 9/2000 | Arai et al. |
| 6,125,193 | A | 9/2000 | Han |
| 6,185,271 | B1 | 2/2001 | Kinsinger |
| 6,212,251 | B1 * | 4/2001 | Tomura et al. .......... 378/15 |
| 6,240,157 | B1 * | 5/2001 | Danielsson ............ 378/15 |
| 6,285,733 | B1 | 9/2001 | Proksa |
| 6,285,740 | B1 | 9/2001 | Seely et al. |
| 6,289,074 | B1 | 9/2001 | Arai et al. |
| 6,292,527 | B1 | 9/2001 | Guendel |
| 6,298,110 | B1 | 10/2001 | Ning |
| 6,324,246 | B1 | 11/2001 | Ruimi |
| 6,379,041 | B1 | 4/2002 | Schuetz et al. |
| 6,381,301 | B1 * | 4/2002 | Massie ................ 378/39 |
| 6,496,558 | B2 * | 12/2002 | Graumann .............. 378/39 |
| 6,504,892 | B1 * | 1/2003 | Ning .................. 378/4 |
| 6,594,338 | B2 | 7/2003 | Darhoux et al. |
| 6,594,342 | B2 * | 7/2003 | Castleberry ........... 378/154 |
| 6,735,274 | B1 * | 5/2004 | Zahavi et al. .......... 378/15 |
| 6,745,066 | B1 * | 6/2004 | Lin et al. ............. 600/425 |
| 6,814,490 | B1 * | 11/2004 | Suhm et al. ........... 378/198 |
| 7,099,428 | B2 * | 8/2006 | Clinthorne et al. ...... 378/17 |
| 2001/0036246 | A1 | 11/2001 | Graumann |

FOREIGN PATENT DOCUMENTS

| | | |
|---|---|---|
| EP | 1 121 899 A1 | 8/2001 |
| WO | WO 00/62674 | 10/2000 |
| WO | WO 02/38045 A2 | 5/2002 |

OTHER PUBLICATIONS

Clinthorne, Neal H., Are Hydrogenated Amorphous Silicon Arrays Usable For Tomographic Imaging, IEEE Transactions on Nuclear Science, Aug. 1994, pp. 1516-1521, vol. 41, No. 4.

Sukovic, Predrag, et al., Design Of An Experimental System For Dual Energy X-Ray CT, IEEE Conference, Oct. 29-30, 1999, Seattle, Washington.

Sukovic, Predrag, et al., Data Weighted vs. Non-Data Weighted Dual Energy Reconstructions For X-Ray Tomography, IEEE Conference, Nov. 8-9, 1998, Toronto, Canada.

Sukovic, Predrag, et al., Penalized Weighted Least-Squares As A Metal Streak Artifacts Removal Technique in Computed Tomography, IEEE Conference, pp. 23-49 to 23-52, Oct. 15-20, 2001.

Sukovic, Predrag, et al., Experimental Results With Dual-Energy Penalized Weighted Least-Squares Image Reconstruction For X-Ray Transmission Tomography, IEEE Conference, Oct. 15-20, 2000, pp. 23-16 to 23-20, Leon, France.

Sukovic, Predrag, et al., Basis Material Decomposition Using Triple-Energy X-Ray Computed Tomography, IMTC Conference, May 24-26, 1999, Venice, France.

Sukovic, Predrag, et al., Penalized Weighted Least-Squares Image Reconstruction For Dual Energy X-Ray Transmission Tomography, IEEE Transaction on Medical Imaging, Nov. 2000, pp. 1075-1081, vol. 19, No. 11.

* cited by examiner

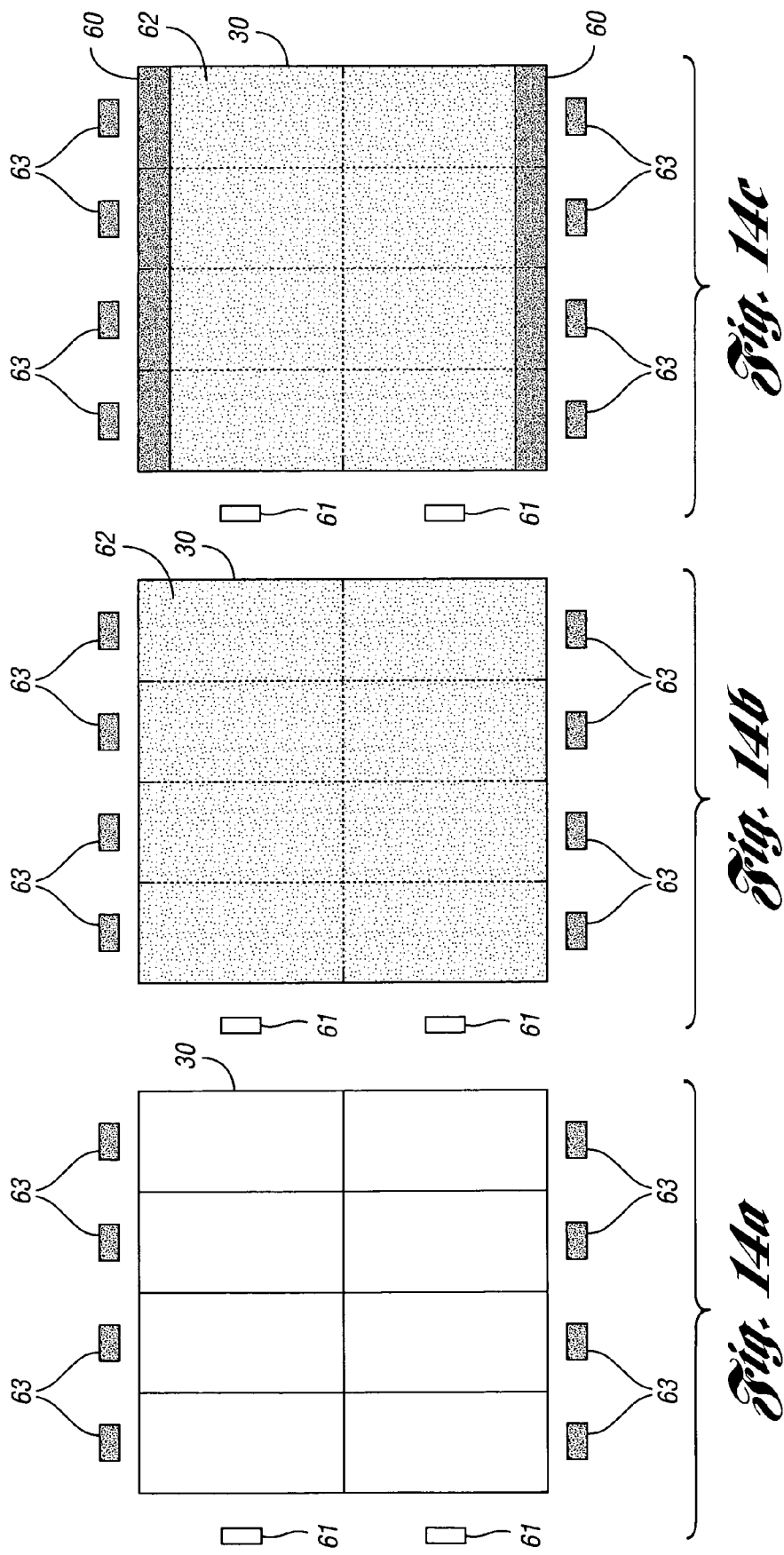

HIGH SPATIAL RESOLUTION X-RAY COMPUTED TOMOGRAPHY (CT) METHOD AND SYSTEM

CROSS-REFERENCE TO RELATED APPLICATION

This application is a continuation of U.S. application Ser. No. 10/183,146 filed Jun. 25, 2002 now U.S. Pat No. 7,099,428 entitled "High Spatial Resolution X-Ray Computed Tomography (CT) System". This application is also related to co-pending application entitled "Method, Processor and Computed Tomography (CT) Machine for Generating Images Utilizing High and Low Sensitivity Data Collected From A Flat Panel Detector Having an Extended Dynamic Range", filed May 29, 2002 and having U.S. Ser. No. 10/157,282, now U.S. Pat. No. 6,868,138.

STATEMENT REGARDING FEDERALLY SPONSORED RESEARCH OR DEVELOPMENT

This invention was made with Government support under NIH Grant No. CA 65637. The Government has certain rights in the invention.

BACKGROUND OF THE INVENTION

1. Field of the Invention

This invention relates to high spatial resolution, X-ray computed tomography (CT) methods and systems.

2. Background Art

The current state of imaging modalities used in these areas of dentomaxillofacial practice, with a particular emphasis on implantology, is described in the following subsections.

Implantology: Pre-Operative and Post-Operative Imaging

The use of dental implants is becoming an increasingly common treatment to replace missing teeth. Successful outcome of the treatment, osseointegration of the implant, depends heavily on precise presurgical planning. Since the functional load in implants can be high, it is important that the implant be placed in a position where it can contact cortical bone and at an angle where the forces are as perpendicular as possible. Selection of the appropriate size and inclination of the implant in both a bucco-lingual and mesio-distal direction requires precise knowledge of the anatomy of the proposed site, including its dimension in all planes, the presence of knife-edge ridges and undercuts, as well as the location of anatomic structures, such as the nasal fossae, the maxillary sinus, and the mandibular canal. An evaluation of the thickness of the cortical bone and the density of the medullary bone is also important to the success of the implant.

Acquiring the information needed for implant treatment planning requires some type of imaging examination. A number of imaging modalities have been used over the years, but they all have limitations and none are completely satisfactory.

Periapical radiography has enough resolution to depict trabecular bone pattern and the floor of the maxillary sinuses, but the images are limited in size and anatomic coverage and often suffer from geometric distortion. In addition, periapical radiographs are only two-dimensional images and do not provide information about the third, bucco-lingual, dimension.

Panoramic radiography is commonly used for implant site assessment because it is readily available, inexpensive, and provides wide coverage of the jaws. However, there are a large number of disadvantages to this technique that limit its usefulness for implant site assessment. The two primary problems are lack of information in the bucco-lingual plane and variability of the degree of magnification in different parts of the image due to changing distance between the rotational center, jaw structures, and film as the X-ray beam rotates around the head. Minor errors in positioning the patient's head in the machine can also exaggerate the degree of enlargement variability, particularly in the horizontal direction. Although dentists frequently try to overcome these magnification problems by having the patient wear a surgical stent with metal markers of a known size during the examination, this device is not adequate to solve all distortion errors.

Conventional (i.e., non-computed, "focal-plane" or "linear") tomography has found an important application in the presurgical examination of proposed implant sites. Its major advantage over periapical and panoramic radiography stems from its ability to show bucco-lingual cross-sectional images. From these cross-sectional images, the dentist can estimate the spatial relationships of anatomic structures, bone height and width, and the inclination of the alveolar processes at the areas into which the implants are to be placed. Numerous studies have demonstrated that conventional tomography can depict the location of important anatomic structures, such as the mandibular canal, more accurately than panoramic radiography. Dimensional measurements are generally reliable with complex-motion tomography, and less so with linear-motion systems.

Conventional tomographs, however, have been reported not to be of diagnostic quality sufficient to allow identification of the canal in as many as 20% of cases. This is primarily due to the unavoidable blur that is inherent in the method, although some canals are poorly corticated and thus would be difficult to visualize with any technique. Another very important disadvantage of conventional tomography is that it is usually necessary to acquire multiple slices to ensure that the region of diagnostic interest is sampled adequately. Because each slice is acquired successively, the process is time-consuming and laborious, thus expensive, and it exposes the patient to a radiation dose that can be high, depending on the number of slices obtained.

X-ray computed tomography (CT) is a more sophisticated method for obtaining cross-sectional images than conventional tomography. It has been considered to be the most reliable technique for the assessment of bone height and width and localization of the inferior alveolar canal, mental foramen, nasopalatine canal, and maxillary sinuses. Consequently, it has been widely recommended for implant planning.

Conventional CT has its drawbacks, however. First, with its merely 2-D reformatted images, it may not clearly depict the inferior alveolar canal. Second, it is time-consuming: conventional CT requires more than 20 minutes to get all the axial slices for a dental implant study. With such a long scanning time, patient fatigue and patient swallowing start blurring the image. Third, conventional CT exposes the patient to a high radiation dose. Fourth, it is expensive. Fifth, it suffers from poor resolution, especially in the z-direction. Sixth, metal streak artifacts can occur in the presence of metallic dental restorations, requiring judicious selection of scan orientation and boundaries to minimize its occurrence.

Spiral CT is one of the most advanced imaging modalities available and is gradually replacing conventional CT. It is primarily used in the areas of medicine that require full body imaging, but is finding its use in dentistry as well. Spiral CT can generate not only 2-D cross-sectional images, but also fully 3-D images. Its 3-D capability is due to the fact that the X-ray source and detector continuously move along a spiral path relative to the body, thus acquiring data that are essentially 3-D. Spiral CT has been successfully used for the pre-surgical assessment for implant treatment planning.

However, the use of spiral CT in dentistry is hampered by its high cost and radiation dose, low spatial resolution in axial direction, and metal streak artifacts. In order to overcome some of the disadvantages, specifically high cost and radiation dose, two dental imaging methods have been proposed: Tuned-Aperture Computed Tomography (TACT™) and Ortho-CT.

TACT™, "an inexpensive alternative to CT," is based on the theory of tomosynthesis. The relatively low cost of TACT is party due to its simplicity and partly due to its use of equipment that already exists at the facility. The use of TACT in implantology has been suggested, but no controlled studies have yet been performed. Nevertheless, its disadvantages in implant planning can be assessed from its characteristics. First, TACT requires the use of fiducial markers to estimate the imaging geometry and perform the reconstruction. This adds to the complexity of operating the instrument. Second, it uses CCD sensors of a low contrast resolution. Third, TACT does no have actual 3-D capabilities, but so-called pseudo-3D; 2-D images are being displayed from different angles, simulating varying projection geometries and providing some perception of three dimensions to the viewer. So, with TACT, the gain in cost-effectiveness is offset by a lower quality scan.

Ortho-CT is another potentially inexpensive alternative to spiral CT. Ortho-CT is basically a small cone-beam CT unit obtained by modifying a maxillofacial radiographic unit called Scanora® (Soredex, Helsinki, Finland) in order to acquire a "partial" CT scan.

In this context, the term "partial CT scan" refers to a cone-beam CT scan using a circular orbit, which, in addition to having the usual cone-beam incompleteness problem (i.e., a circular orbit does not satisfy Tuy's completeness conditions), is more incomplete in the sense that the data is insufficient for quantitatively reconstructing 3-D cross-sectional images to the use of a detector and scan geometry that do not measure all necessary rays through the object.

As an example, the "fan-beam scan" or central slice of the circular-orbit cone-beam scan is complete if the detector and scan geometry measure all parallel rays through the object at angles ranging from 0 to 180 degrees.

In the Ortho-CT device, a complete set of parallel rays is not measured at any view angle. It has a good spatial resolution; the resolving power at an MTF of 0.5 can be 1 lp mm$^{-1}$ and the visual resolution limit about 2.0 lp mm$^{-1}$. Radiation dose is low; skin dose is almost the same as with panoramic radiography and several dozen times lower than with conventional CT.

However, the applicability of Ortho-CT in implant planning is limited for four reasons. First, it can image only small areas (32×38 mm). If a larger area needs to be imaged, multiple scans are required. Second, its contrast resolution is so low that Ortho-CT is incapable of discriminating soft tissue. Third, its values are only relative and do not correspond to the absolute values of bone density. This is a consequence of its use of incomplete data. Fourth, although its behavior in the presence of metal fillings has not been reported on, it is expected that it suffers from metal streak artifacts.

In addition to presurgical planning of implants, there is a need for long-term maintenance and monitoring of tissue health around the implant after surgery has been performed. Peri-implantitis can progress around dental implants in a manner similar to the progression of periodontitis around natural teeth. If the determination of a failing implant could be made before the implant actually fails, therapeutic intervention might prevent further deterioration of implant support and loss of the implant. A long-standing goal of peri-odontal research is to find a diagnostic tool with a high sensitivity for detecting subtle disease activity around teeth. In particular, the detection of subtle changes in bone mass may be of great value for evaluating progressive periodontal disease or bone gain/loss after therapy.

Conventional radiography is routinely used by periodontists for the postsurgical assessment of the implant. It can display the mesial and distal aspects of the implant site, but it provides little information about the facial and lingual aspects of the implant site because of the obscuring effects of the radiopaque implant material. Its other major limitations include the subjective interpretation of the radiographic image, lack of sensitivity, and the inability to quantify bone mass.

Digital subtraction radiography can quantify bone mass and thus can be used for postsurgical implant assessment. The method involves taking two separate radiographic scans and then subtracting them. The two images are made at different times and must be as identical as possible. The exposure factors and processing parameters that affect density and contrast must be consistent between the two scans and the projection geometry must be duplicated as nearly as possible All this makes the method laborious and inefficient, especially when the medium is film, which is often the case. Finally, it cannot overcome the obscuring effects of a metal implant sufficiently to allow reliable detection of facial and lingual bone loss at implant sites.

The Temporomandibular Joint (TMJ)

When a patient presents complaints referable to the TMJ region, the findings from the clinical examination may indicate the need for imaging to aid in diagnosis and treatment planning. The osseous structures can be visualized with a variety of imaging techniques, including plain and panoramic radiography, conventional tomography and CT, depending on the degree of detail required.

Conventional tomography plays a significant role in TMJ imaging. Tomographic studies in the lateral and coronal planes demonstrate osseous components of the joint, whereas arthrotomographic examinations provide information about the status of the soft-tissue intra-articular disk. However, tomography of the TMJ is technically demanding because the imaging protocol must be customized for each patient due to the variability of condylar angles. Images made with linear-motion machines may also be suboptimal due to streaking artifacts and incomplete blurring of adjacent structures.

The use of computed tomography for TMJ imaging has generally been reserved for complex cases as a result of its relatively high cost and high radiation dose. Evaluation of articular disk position and function is usually performed with magnetic resonance imaging or arthrotomography, again both expensive techniques.

Detection of Facial Fractures

Another important problem in dentistry is the determination of the location and displacement of facial fractures in patients who have suffered trauma to the maxillofacial region. Complex trauma to the facial skeleton requires both highly qualified clinical knowledge and an accurate imaging technique.

Conventional radiography is unsuitable for the task because it requires multiple scans to obtain all the views that are necessary for evaluation. Even with a series of radiographs, it is sometimes difficult to detect subtle fractures. And conventional tomography, while theoretically capable of demonstrating complex anatomy better than planar projection radiographs, has generally been superseded by CT in most hospitals.

Spiral CT imaging is a better solution for detection of facial fractures. Only one spiral CT scan is needed for the examination, and it does not require movement of the patient to obtain multiple views. It is very fast and can scan the entire midface and the frontal sinus in less than a minute. Thus, it allows the diagnostician to move on to other essential diagnostic and therapeutic interventions without delay. Also, it allows for further processing of the data without requiring the patient's continued presence in the CT unit. Finally, spiral CT produces images of superior quality and can be used to generate 3-D images that can be rotated on a video screen to demonstrate the anatomy and pathology from all angles.

However, the use of spiral CT for detecting facial fractures has drawbacks. It is costly and it exposes the patient to a high radiation dose. It also suffers from metal streak artifacts, which can result in misleading scans of the facial complex.

Lesions and Diseases of Soft Tissue in the Head and Neck

In addition to imaging of the bony structures of the maxillofacial complex, a very important task is the imaging of the soft tissues in the head and neck. Particularly important is imaging of inflammations, cysts, and tumors.

While conventional radiography produces adequate bone images, it provides little information regarding soft tissues as a result of the inability of film-screen systems to record X-ray attenuation differences of less than 2%.

CT, however, is much more effective at separating subtle tissue contrast difference (as low as 0.5%). CT can differentiate not only soft tissue from bone, but also various types of soft tissues from each other. Consequently, CT has found a very important application in the evaluation of the presence and extent of clinically suspected pathology in the head and neck, including tumors, cysts, and inflammations. When additional information concerning the soft tissues is required, an intravenous contrast agent can be used. Cavalcanti et al. have successfully used spiral CT to measure the volume of oral tumors.

Although CT has proven superior in many aspects to other modalities in this application, its use has been limited by three factors: cost, radiation dose and metal streak artifacts. In addition, the spatial resolution available in current CT scanners, which are designed primarily for full-body imaging, may not be optimal for lesions in the head and neck.

MRI has also been used to image soft tissue of the head and neck. Some advantages of MRI over CT include better contrast resolution, absence of artifact degradation from dental restorations, visualization of major vessels without intravenous injection of contrast material, and direct, three-plane imaging without patient repositioning. MRI, however, is more expensive than CT, and requires a longer time to obtain a scan. To date, there is no general consensus about which imaging technique is optimal for use in diagnosis of lesions in the head.

Reconstructive Facial Surgery

Surgery of craniofacial deformities is a complex task that requires careful preoperative planning and specific, detailed information on patient's pathology and anatomy. The goals of maxillofacial surgery are not limited to treating the condition of bone, but extend to improving both the morphology and function of soft tissues, such as facial appearance for the patient. It is necessary, therefore, to ascertain how the proposed alteration of bone will affect the form and function of the surrounding soft tissue. Effective planning of reconstructive facial surgery requires not only adequate imaging of the bone and soft tissue but also the means of interpreting these images in combination to predict how the surgical alteration of bone will affect soft tissue.

Radiography has been used with a certain amount of success for planning facial reconstructive surgery. However, facial reconstructive surgery presents a three-dimensional problem of anatomical rearrangement and cannot be effectively planned using two-dimensional images. Morever, some facial and skeletal anomalies, specifically those involving facial asymmetry, are not amenable to analysis using only two-dimensional images.

CT and MRI can supply detailed, three-dimensional information on the patient's anatomy, and have therefore become the methods of choice in maxillofacial surgery planning. They are typically used in conjunction with computer software that shows the predicted three-dimensional rendered postoperative facial surface. However, both are expensive. In addition, CT suffers from metal streak artifacts and exposes the patient to a high radiation dose while MRI is not particularly useful for examining bony structures.

Several devices have been conceived for dentomaxillofacial imaging. Ortho-CT is a vertically oriented device that acquires a partial CT scan, and while spatial resolution is adequate, the device suffers from artifacts due to the incomplete nature of the scan and does not produce quantitatively accurate estimates of attenuation (necessary for assessing bone quality).

TomCAT is a cone-beam imaging device in which the patient lies supine on an imaging table similar to conventional spiral or single-slice CT instruments. The TomCAT uses an image intensifier and CCD camera for the detector—a combination that has relatively poor dynamic range (reducing quantitative accuracy) and also suffers from spatial distortions. Although images reconstructed from TomCAT have spatial resolution similar to conventional general-purpose CT instruments, contrast resolution is quite poor and images appear to suffer from a great deal of X-ray scatter (and perhaps veiling glare from the image intensifier).

Individual methods are known to be close to the techniques described herein (e.g., Wagner's method for scatter estimation and correction).

The following U.S. patents are deemed to be relevant to the present invention: U.S. Pat. Nos. 5,390,112; 5,615,279; 6,018,563; 5,909,476; 6,118,842; 6,075,836; and 5,999,587. The following U.S. patents are deemed to be of less relevance to the present invention: U.S. Pat. Nos. 5,927,982; 6,094,467; 6,125,193; 5,461,650; 4,812,983; 4,590,558; 4,709,333; 5,243,664; 5,798,924; 6,035,012; 5,293,312; 5,390,112; 5,615,279; 5,644,612; 5,751,785; 5,042,487; and 5,909,476. The following U.S. patents are also deemed to be relevant: U.S. Pat. Nos. 5,778,045; 5,793,838; 5,805,659; 5,815,546; 5,864,146; 5,878,108; 5,881,123; 5,903,008; 5,921,927; 5,949,846; 5,970,112; 5,995,580; 6,052,428; 6,101,234; 6,101,236; 6,104,775; 6,118,841; 6,185,271B1; 6,285,733B1; 6,285,740B1; 6,289,074B1; 6,292,527B1; 6,298,110B1; 6,324,246B1.

SUMMARY OF THE INVENTION

An object of the present invention is to provide an improved high spatial resolution X-ray computed tomography (CT) method and system.

In carrying out the above object and other objects of the present invention, a high spatial resolution X-ray computed tomography (CT) system is provided. The system includes a support structure including a gantry mounted to rotate about a vertical axis of rotation. The system further includes a first assembly including an X-ray source mounted on the gantry to rotate therewith for generating a cone X-ray beam and a second assembly including a planar X-ray detector mounted on the gantry to rotate therewith. The detector is spaced from the source on the gantry for enabling a human or other animal body part to be interposed therebetween so as to be scanned by the X-ray beam to obtain a complete CT scan and generating output data representative thereof. The output data is a two-dimensional electronic representation of an area of the detector on which an X-ray beam impinges. A data processor processes the output data to obtain an image of the body part.

The second assembly may include a grid positioned adjacent the detector to reduce scatter.

The first assembly may include a shadow mask for spatially modulating the source and to estimate residual scatter.

The X-ray source and the X-ray detector may be mounted on the gantry to rotate therewith along an elliptical path.

The first assembly may be capable of irradiating the body part with two different X-ray spectra.

The first assembly may further include a source collimator mounted adjacent the X-ray source.

The system may further include a scatter rejection collimator mounted on the gantry to rotate therewith.

The system may further include a device for controlling position of the source collimator based on position of the detector relative to the source.

The detector may include a converter for converting X-ray radiation into visible light.

The detector may further include a hydrogenated amorphous silicon (aSi:H) detector array.

The data processor may be programmed with a statistical image reconstruction (SIR) program.

The entire body part may be scanned by the X-ray beam in a single scan.

The processor may be programmed with a penalized weighted least squares (PWLS) reconstruction program.

The processor may further be programmed with a dual energy penalized weighted least squares (DE PWLS) reconstruction program.

The detector may generate high and low energy data at each rotation angle of the gantry.

The processor may be programmed to obtain the high and low energy data from the detector and generate the image using the obtained data.

The system may further include means for correcting for body part motion at each rotation angle of the gantry.

The means for correcting may include a device that measures relative motion of the body part to obtain measurement data. The processor may be programmed with an image reconstruction program which utilizes the measurement data.

The body part may be a head, and the system may be a dentomaxillofacial system.

The gantry may be mounted to move vertically along the axis of rotation.

The gantry may be mounted to pivot along an accurate path about a point on the axis of rotation.

The system may further include a device for offsetting the detector in a plane substantially perpendicular to the axis of rotation relative to the gantry.

The system may further include an arm coupled to the detector and the source collimator for controlling position of the source collimator based on position of the detector.

The system may further include means for stabilizing motion of the head.

Various imaging modalities have been used in the dentomaxillofacial fields over the past few decades—none with entirely satisfactory results. The system described herein will find its most immediate use in pre-operative site assessment for dental implants and in post-operative assessment of a failed implant. It is further anticipated that the system will lead to the advancement of scientific knowledge and enable further discoveries in TMJ imaging, detection of facial fractures and lesions and diseases of the soft tissue in the head and neck, and imaging used in reconstructive facial surgery.

The above object and other objects, features, and advantages of the present invention are readily apparent from the following detailed description of the best mode for carrying out the invention when taken in connection with the accompanying drawings.

BRIEF DESCRIPTION OF THE DRAWINGS

FIGS. 14a-14c illustrate detector masking so that a "dark signal" is present along each data line even with illumination of the detector with the X-ray source; resulting values from pixels within this region can be used to correct voltage offset or "pedestal" for every detector element on a particular data line; FIG. 14a is a back view of the detector; FIG. 14b is a front view with a scintillator layer; and FIG. 14c is a front view with absorbing strips.

DETAILED DESCRIPTION OF THE PREFERRED EMBODIMENTS

A system of the present invention possess a wide spectrum of properties to be used effectively both in implantology and for the applications described. The properties are summarized below in Table 1.

TABLE 1

1. High contrast-resolution for both bone and soft tissue;
2. High spatial resolution in X, Y, and Z directions;
3. Low radiation dose;
4. Metal streak artifacts removal;
5. Quantification of soft tissue and bone densities and their changes;
6. Full 3-D capabilities;
7. Ability to generate axial, coronal, sagittal, and oblique planes images;
8. Ability to produce undistorted images with linear measurements preserved;
9. High scanning speed to avoid body movement artifacts;
10. Relatively inexpensive; and
11. Easy to use.

None of the previous dentomaxillofacial imaging modalities possesses all these properties, and the practitioner has historically been face with various trade-offs in the decision as to which modality to use.

The new system features all the properties from Table 1, and is therefore expected to become the modality of choice in dental implantology and other clinical tasks that involve the dentomaxillofacial complex.

Figure 1A:
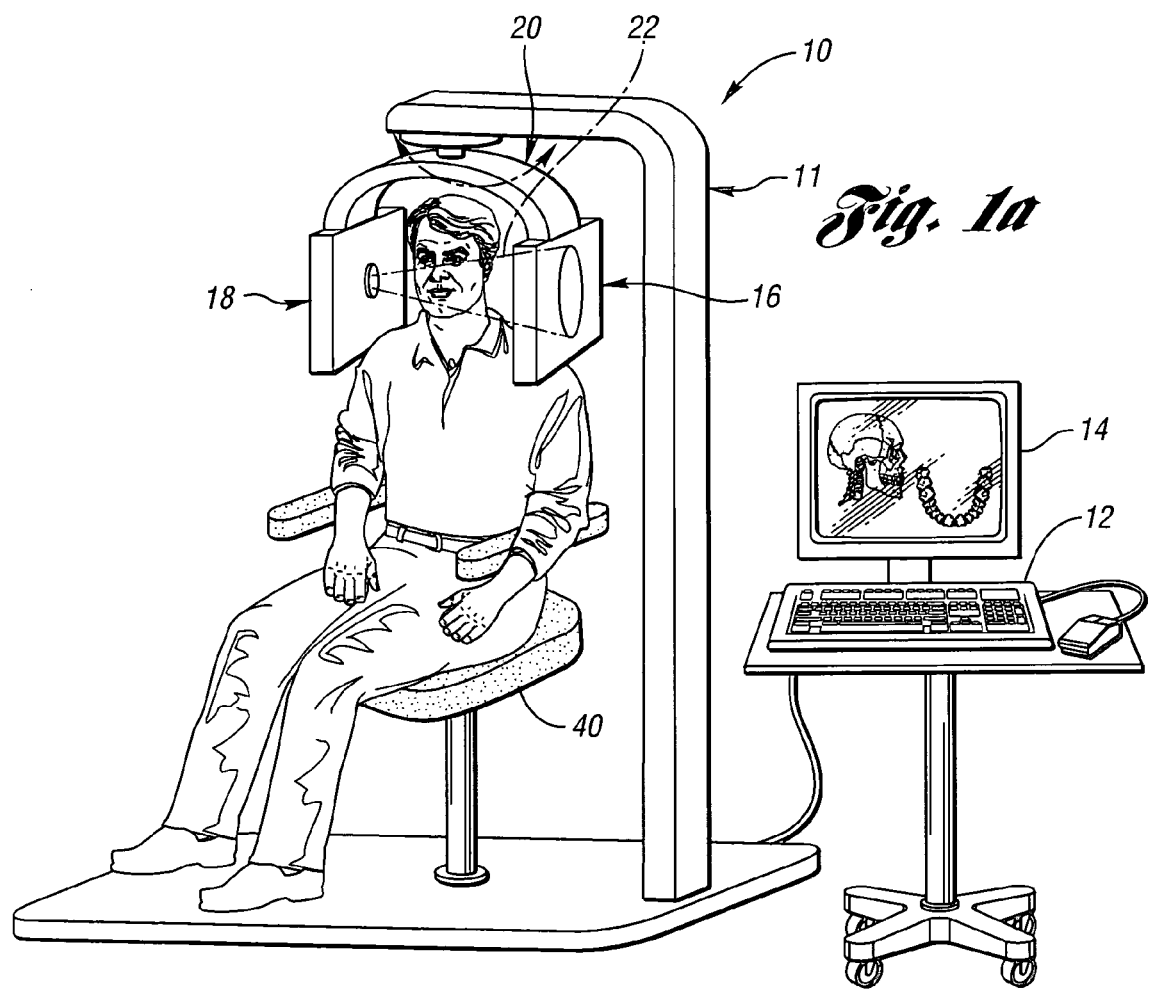
FIG. 1a is a schematic view of a system constructed in accordance with the present invention wherein a patient is seated in a chair (a chin-rest is not shown); the system features cone-beam geometry, aSi:H detector array, and PWLS and DE PWLS reconstruction methods.

A preferred system of the invention is generally indicated at 10 in FIG. 1a. Its building blocks are: 1) a cone-beam data acquisition and image reconstruction devices including a computer 12 with a display 14; 2) a detector assembly, generally indicated at 16, including an amorphous silicon (aSi:H) detector array coupled to a source assembly, generally indicated at 18, including an X-ray source, both assemblies being mounted on a rotating gantry, generally indicated at 20, and fitted with appropriate X-ray filtration, collimation, shadow masks, etc.; 3) the computer 12 or data processor is programmed with a) a penalized weighted least squares (PWLS) reconstruction program and/or b) a dual energy penalized weighted least squares (DE PWLS) reconstruction program when precise information regarding soft tissue and bone densities is needed.

Cone-Beam Geometry

Compared to the conventional fan-beam geometry, a cone-beam geometry is used in the present invention due to its high efficiency in X-ray use, inherent quickness in volumetric data acquisition, and potential for reducing the cost of CT machines. Conventional fan-beam scans are obtained by illuminating an object with a narrow, fan-shaped beam of X-rays. The X-ray beam generated by the tube is focused to a fan-shaped beam by rejecting the photons outside the fan, resulting in a highly inefficient use of the X-ray photons. Further, the fan-beam approach requires reconstructing the object slice-by-slice and then stacking the slices to obtain a 3-D representation of the object. Each individual slice, therefore, requires a separate scan and separate 2-D reconstruction.

The cone-beam technique, on the other hand, requires only a single scan to capture the entire object with a cone of X-rays 22. The time required to acquire a single cone-beam projection is the same as that required by a single fan-beam projection. But since it takes several fan-beam scans to complete the imaging of a single object, the acquisition time for the fan-beam tends to be much longer than with the cone-beam. This is important because the more time the patient is subjected to the scanning process, the more likely it is that the patient may move or swallow, blurring the scan. Although it may be possible to reduce the acquisition time of the fan-beam method by using a higher power X-ray tube, this increases the cost and bulkiness of the scanner.

Hydrogenated Amorphous Silicon Detector (aSi:H) Arrays

The imaging detector 16 used in the system 10 is a large-area array constructed from hydrogenated amorphous silicon (aSi:H) as described in the above-noted application. The detector 16 is a "self-scanned" array of n-i-p photodiodes and thin-film transistor switches. The integrated-flux mode X-ray detector 16 is constructed by mating a flat-panel photodiode array with the appropriate scintillator.

The detector 16 is both inexpensive and capable of generating high-quality images. Essentially the same technology is used to construct active-matrix, flat-panel computer displays and large-area document imagers. They are replacing film and image-intensifiers in conventional radiography and fluoroscopy applications. Several companies currently produce detector arrays for commercial sale. Several years ago it was predicted that these devices could be used for tomography and for attenuation correction applications in PET and SPECT.

Although it has been recently suggested that a special image intensifier can be coupled with a CCD camera for use in a cone-beam-based dental CT scanner, the characteristics of aSi:H-based flat panel detector arrays make them a much better choice for this application. The aSi:H detector arrays offer three distinct advantages. First, the aSi:H flat panel detectors, unlike image intensifiers, do not create geometric distortions that must be addressed when processing the data. Second, flat panel detectors are available in sizes up to 40×40 cm, which is large enough to cover the entire head, whereas image intensifiers have relatively smaller diameters, creating "truncated view" artifacts. Third, flat panel detectors afford a greater dynamic range than that offered by the image intensifier+CCD camera approach.

The a-Si photodiode array/scintillator combination is not the only type of flat-panel imaging detector that can be used in the system 10 described here. In particular, direct detection arrays, which have an X-ray converter such as lead iodide or amorphous selenium (or other suitable converter), can be used. These devices have no intermediate light conversion step and instead convert X-rays to an electrical charge that is read out by the array. Although direct detection devices may eventually offer advantages such as higher spatial resolution, they are at present investigational having detection efficiency that is too low at the energies used in tomography applications.

Figure 1C:
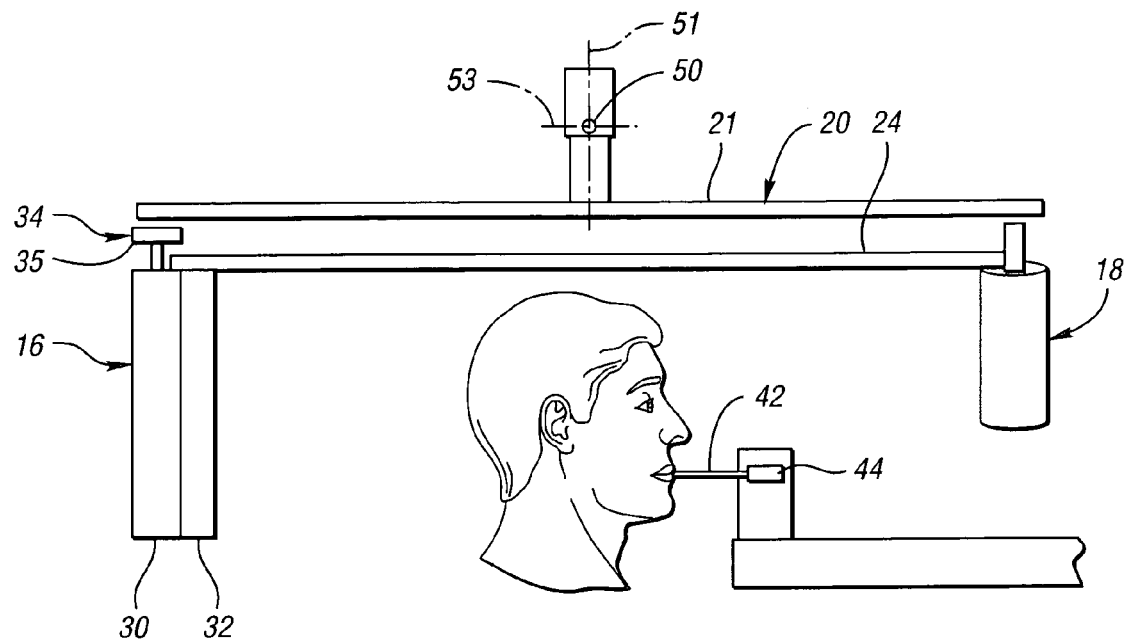
FIG. 1c is a schematic view of a head motion detection subsystem of the present invention.
Figure 2:
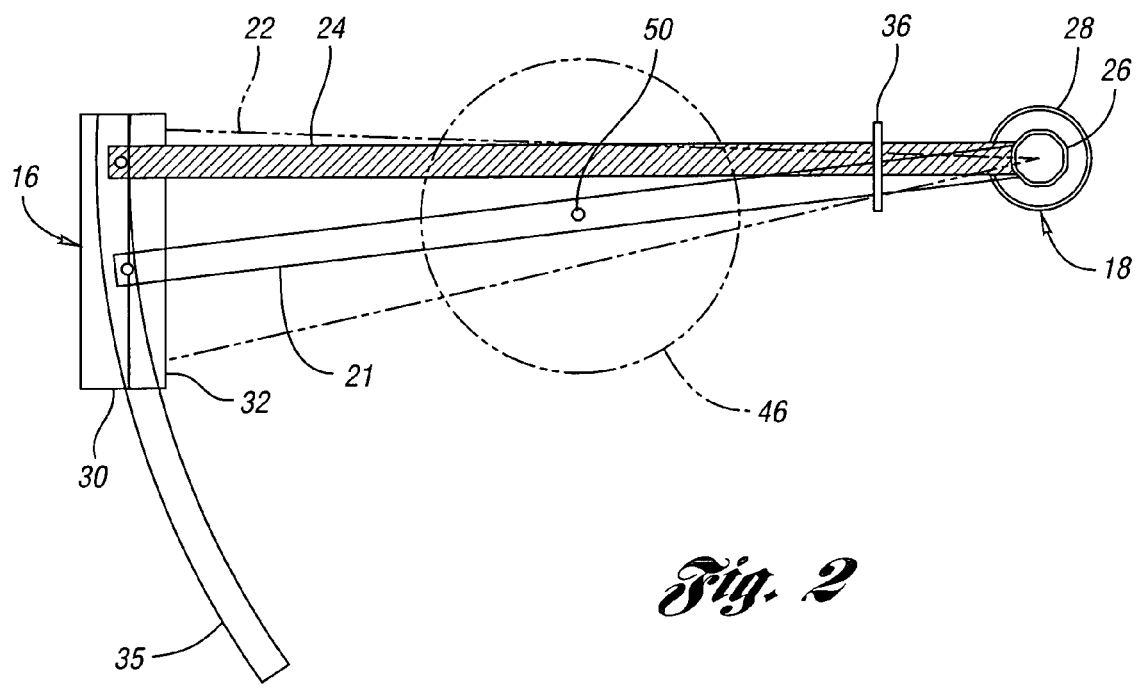
FIG. 2 is a bottom view of a rotating arm portion of the gantry of the present invention; source, source collimator, detector, shadow mask, and detector translation track are illustrated; detection position controls position of source collimator through a mechanical arm such that only the appropriate portion of a patient's head or neck is irradiated with X-rays.
Figure 3:
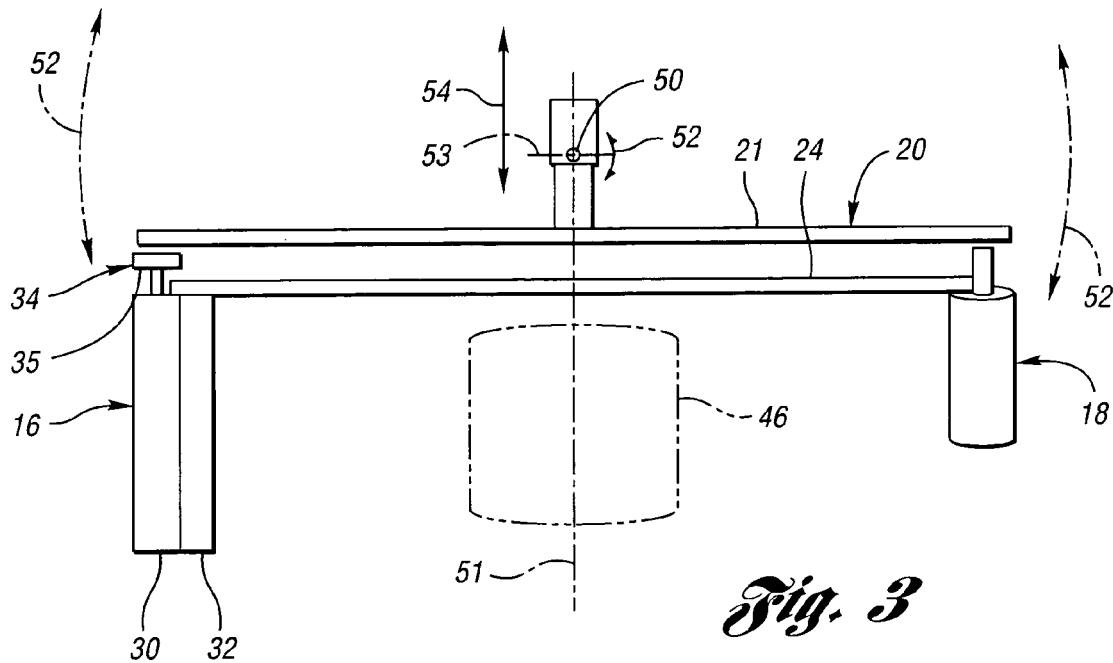
FIG. 3 is a side view of the rotating arm portion of the gantry shown in FIG. 1; the entire arm can either move up or down vertically (in addition to rotating) or can pivot about the point shown so that a "complete" tomographic dataset can be acquired.

The vertically-oriented, high-resolution tomograph system 10 is primarily provided for dentomaxillofacial imaging applications. The basic system 10 includes a support structure, generally indicated at 11, including the gantry 20 having an arm 21, which, in this case, adjusts to accommodate different size patients and a rotating arm (as shown in FIGS. 1c, 2 and 3 at 24) to which is affixed an X-ray source 26 and a controlled source collimator 28 (i.e., FIG. 2) of the assembly 18 on one end of the arm 24 and on the other end of the arm 24, the assembly 16 including a 2-D position-sensitive X-ray detector 30 and a scatter-reducing collimator 32. The system 10 also includes a device, generally indicated at 34, for moving the detector 30 with respect to the arm 21 to accommodate different patient head sizes and to reduce the effect of detector non-uniformities. The device 34 includes a detector translation track 35. In order to acquire images that quantitatively assess the quality (i.e., mineral content) of bone, the instrument can switch between two X-ray tube potentials or an X-ray filter 36 can be interposed that spatially modulates the source (i.e., a "shadow mask"). At each rotation angle of the gantry arm 21, the X-ray source 26 irradiates the object with two different X-ray spectra and two images are recorded from the detector 30.

More detailed drawings of the assemblies 16 and 18 are shown in FIGS. 2 and 3 wherein the detector 30 is translated along the track 35 to various offset positions and the position of the detector 30 controls the position of the source collimator 28 by the use of the mechanical arm 24. The purpose of these features are discussed hereinbelow.

To accomplish scanning, the patient sits upright in a chair 40 of the support structure 11. The chair may be vertically adjustable. The patient may, for purposes of reducing head-motion during the scan, bite into an immobilizing apparatus 42 (i.e., FIG. 1c) affixed to the tomograph (e.g., a dental impression tray filled with impression material as used in conventional linear tomography). During set-up for the scan, the operator preselects the desired X-ray tube (i.e., source) potential (kV) and the instrument performs a "scout scan" as described in more detail below. From the scout scan, not only can the optimum exposure time for each frame be estimated (as it is done in current practice), but the appropriate detector offset can also be computed. In order to acquire a dataset that is tomographically complete, the offset allows use of a detector that is smaller than would be ordinarily necessary to collect a tomographically complete dataset of the entire head (complete with respect to the "fan-beam" slice). It also provides the desirable added feature of reducing detected scatter as described below.

Correction for the Head Motion

Although the instrument may utilize a device to stabilize the motion of the patient's head, such as the bite plate, as illustrated in FIG. 1c at 42, it is nonetheless expected that the patient will still slightly move during the scan (which will typically last between 30 and 90 seconds). This residual head motion will cause the data acquired at different angles to be inconsistent with each other, thus introducing artifacts in the reconstructed images. These artifacts, referred to as "patient motion artifacts," typically result in images that are blurred. In its mild form, the blurring effectively reduces the spatial resolution of the device, while in severe cases it can render the image useless, and needs to be corrected for as the spatial resolution is at premium in the imaging of the dentomaxillofacial complex.

A solution for correcting the head motion artifacts will now be described. The method consists of two parts: 1) a device that measures the relative motion of the head at each projection; and 2) software method that incorporates these measurements into image reconstruction.

The head is treated as a rigid body with six degrees of freedom. The motion of the head is measured with a device depicted in FIG. 1c. It consists of a sensor 44 that records the motion of the head. The recordings of the device are synchronized with the image acquisition sequence of the detector 30 so that for each detector position, the position of the head is known.

These measurements are then fed into the computer 12 programmed to perform the image reconstruction method. The movement of the head in the coordinate system of the scanner can be looked at as the (equivalent in magnitude but opposite in direction) movement of the scanner (source 26 and detector 30) in the coordinate system of the head. The expressions for all image reconstruction algorithms (e.g., filtered back projection, statistical image reconstruction methods, etc.) are typically written in the coordinate system of the reconstructed object (in our case the head) and involve the coordinates of the X-ray source 26 and detector 30 in this coordinate system. In the proposed method, these coordinates of the X-ray source 26 and detector 30 are different at each angle, where the difference corresponds to the measured head motion.

Dual-Energy Imaging for Bone-Quality Assessment

In addition to single-energy scanning, where as in conventional instruments attenuation measurements through the object are taken using a single X-ray spectrum, the system of the present invention is capable of acquiring and processing data using two X-ray spectra. The advantages are two. First, it is well known that the technique can provide superior corrections for "beam-hardening" or the fact that the effective energy of the broadband X-ray bremsstrahlung radiation increases as the X-ray beam traverses soft tissue and bone and the lower energy X-rays are preferentially absorbed.

Second, the method, when combined with the appropriate image reconstruction technique (e.g., Penalized Weighted Least Squares), can provide good estimates of bone-mineral contact as a measure of bone quality (which is especially important in dental implantology).

There are numerous methods for accomplishing imaging using two spectra. A potentially important technique can generate two spectra by spatially modulating the X-ray beam using a "shadow mask." This device, a filter 36 that spatially modulates the X-ray beam, has been used in order to acquire dual-energy data simultaneously. The shadow mask 36 used here, however, can contain both filtration elements for dual-energy data acquisition as well as "beam-stops" for estimating residual scatter (see below).

Complete Cone-Beam Scan Orbits

To acquire a set of cone-beam projection data that satisfies the cone-beam completeness conditions, the focal-spot of the X-ray source should intersect every plane through the object. Obviously, a circular orbit does not satisfy these conditions (although usable CT images have been obtained with circular orbits). There are a number of simple orbits that can be used with the described device to satisfy these conditions.

As two examples, the source 26 and the detector 30 can move axially during rotation to accomplish helical cone-beam scanning or the source 26 and the detector 30 can "wobble" to such an extent that the focal-spot of the source 26 intersects every plane passing through the desired axial extent of the scan (FIG. 3). This additional motion can be accomplished in a variety of ways from using an additional motor to move the gantry 20 vertically or wobble it during rotation by using a mechanical cam arrangement (no shown) that transfers some of the torque of the motor used to rotate the gantry 20 into the appropriate force.

FIG. 3 shows an optional pivot 50 on vertical axis of rotation 51 for gantry movement as indicated by arrows 52. Alternatively, the gantry 20 moves vertically as indicated by arrows 54.

Figure 1B:
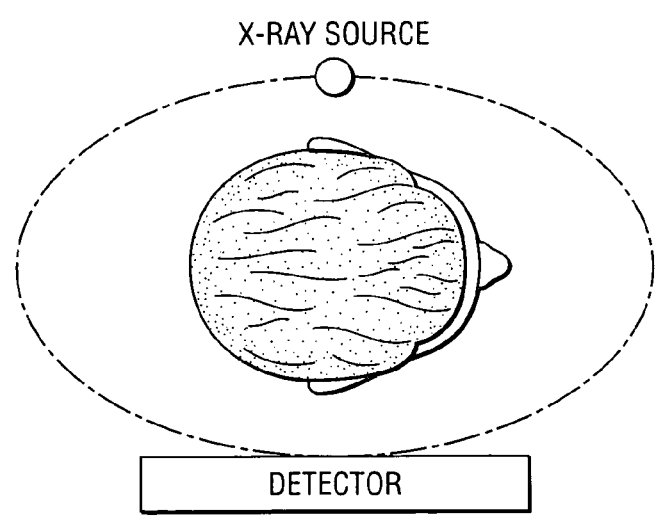
FIG. 1b is a schematic view illustrating an elliptical sensing orbit of an X-ray source and a detector of the present invention.

The system 10 is capable of scanning a head along an elliptical orbit, as shown in FIG. 1b. An elliptical orbit is better suited for head imaging as the head is typically elliptical in shape. This is of particular interest when an offset detector arrangement is used as described herein. The elliptical arrangement allows the detector 30 to capture more data while moving along the sides of the head in comparison to a circular scan. The data acquired in this fashion is then fed into the data processor or computer 22 programmed with a modified image reconstruction program.

Using a "Scout-Scan" to Estimate Exposure and Determine Best Detector Offset

It is common practice to use a low-current scan at the desired X-ray tube potential in order to determine whether patient positioning is proper and to estimate an appropriate exposure. In addition to using the scout scan for these purposes, the system 10 of the invention also uses the scan to determine an appropriate offset for the detector 30 in order to (1) ensure that a complete dataset is acquired, (2) ensure that enough information is available to calculate detector positions such that the tradeoff between X-ray scatter and improved information resulting from measuring some rays twice is appropriate.

Using an Offset Detector to Reduce Necessary Size, Improve Sampling and Decrease X-Ray Scatter The system 10 is capable of using a detector having a width smaller than that ordinarily required to obtain a complete tomographic dataset. Typically, in fan-beam and cone-beam tomography, the X-ray image or projection of the object in each view must encompass the entire object. This, depending on the system geometry, can require use of a detector that is quite large, which increases system cost. It is well known that a detector of smaller size can be used. Specifically, a detector half of the width can be used along with a single rotation plus an angle equivalent to the cone-angle to acquire a dataset that is essentially complete (in the sense that it contains the same data contained in the scan using a full-size detector for the central slice). Data from the half-detector geometry can be reconstructed using a modified image reconstruction algorithm.

In addition to cost-savings of using such an arrangement, the detector 30 can be combined with source collimation to irradiate only the portion of the object containing line segments connecting the source 26 with the detector 30. This arrangement, as noted below, will reduce X-ray scatter.

Rather than using a detector having a fixed offset, as has been used previously, the detector 30 in this system 10 can move along the track 35 (FIG. 2 wherein a field of view of the system 10 is indicated at 46) to achieve a variable offset in order to collect a complete dataset. The offset of the detector 30 can either (1) be predetermined and set once per scan by the operator, or (2) be moved by motor control to positions determined from the scout scan or from previous frames of the diagnostic scan. The advantage of this approach is that the detector 30 can be optimally positioned for each object scanned. For example, the detector 30 may be of such a size that projections of the object "almost" fit the width. In this case, the detector 30 may not need to be displaced by a half-detector width. The advantage for doing so is that some portions of the object will be sampled twice by the X-ray source 26 and the detector 30 during the scan reducing noise due to the quantum nature of X-ray detection.

Figure 4:
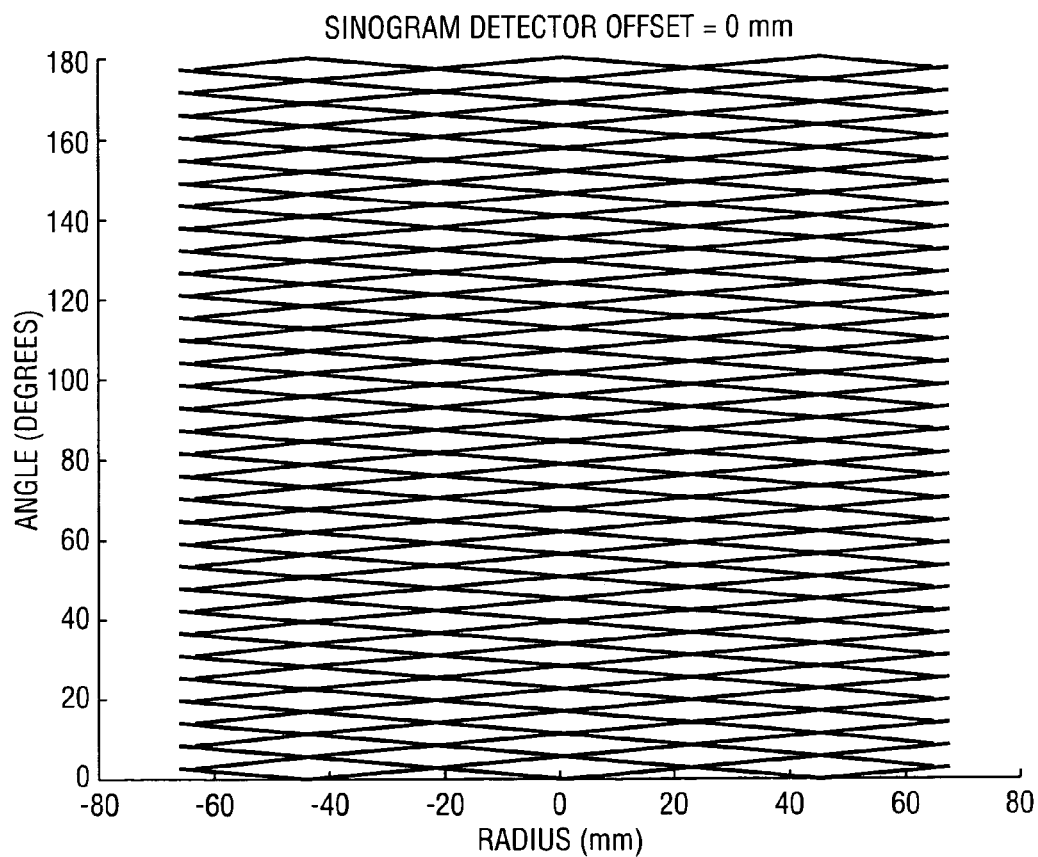
FIG. 4 is a graph which shows a sinogram sampling pattern for the fan-beam slice of a device with no detector offset; each sinogram position (angle and radius) is essentially sampled twice.
Figure 5:
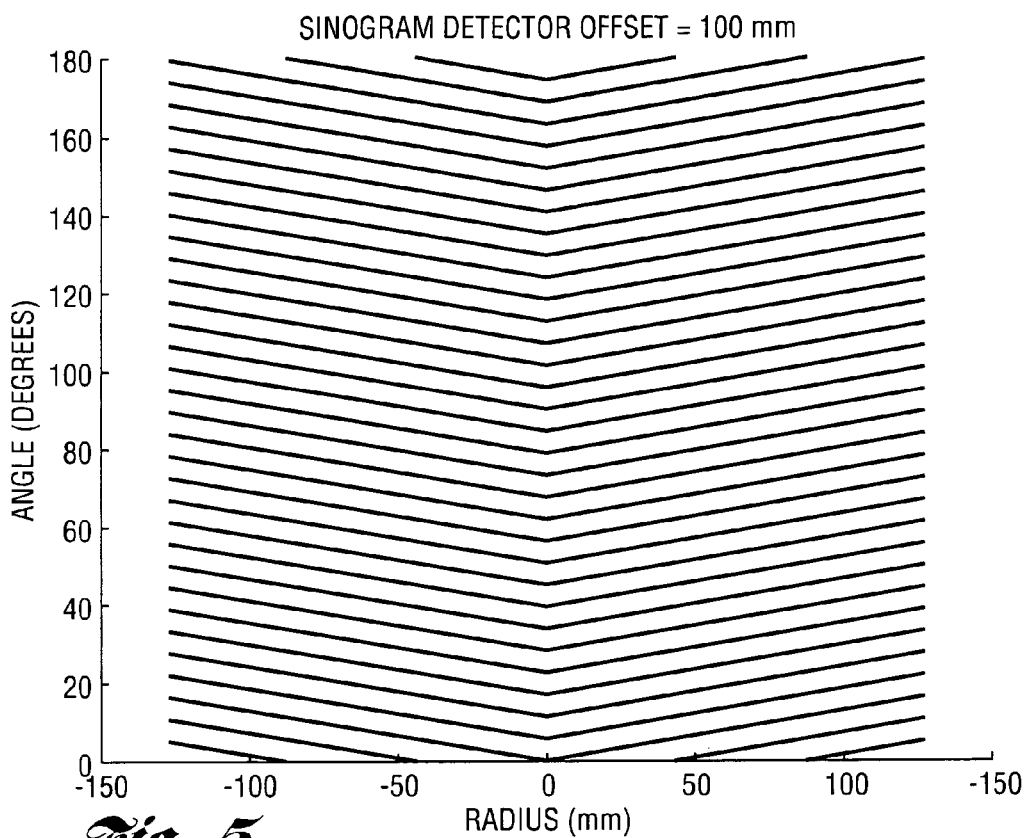
FIG. 5 is a graph which shows a sinogram sampling pattern with detector offset equal to one-half the detector width; in this case, each position in the sinogram is sampled once (or relatively the same number of times as for the detector at zero offset); size of the field-of-view, however, is considerably larger.
Figure 6:
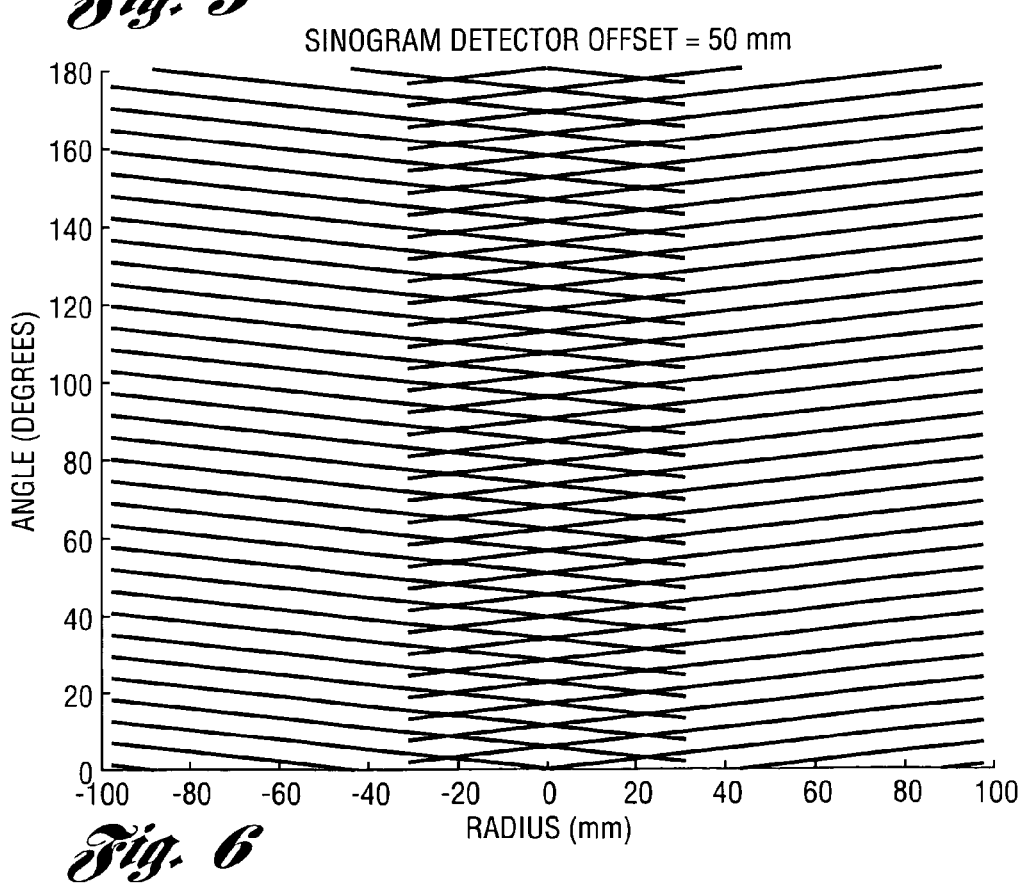
FIG. 6 is a graph which shows a sinogram sampling pattern with the detector at an intermediate offset position; in this case, the size of the field-of-view is greater than that for the detector at zero offset and rays nearer the center of the object (the thickest part, generally) are sampled twice while those nearer the periphery only once; this has the effect of improving the signal-to-noise characteristics of the data and is similar, although not exactly the same, as use of a bowtie filter in conventional CT.

FIGS. 4-6 show examples of the sinogram sampling pattern of the fan-beam slice for detector offsets ranging from none to one half-detector width. When the detector 30 has no offset, the entire sinogram is sampled twice. At full offset, it is only sampled once per rotation. At positions between these extremes, a portion of the object (generally the thickest part) is sampled twice, which can reduce noise.

First-Order Scatter Reduction Using a Coarse, High-Transparency Detector Grid

Scattering—both Compton and coherent—is the most prevalent interaction mechanism of X-ray photons with tissues of the body. While scattering contributes significantly to the observed attenuation of a beam of X-ray photons through the body, a large fraction of the scattered photons escape the body and are subsequently detected at the X-ray detector. Recording these photons, whose direction has been altered considerably from the incident X-ray beam, leads to serious reductions in the contrast-resolution of X-ray CT.

In conventional fan-beam or spiral-scan tomography, Compton-scatter is reduced by two methods: 1) the X-ray source is finely collimated so that it only illuminates a narrow region subtended by the strip-detector (either single- or multi-slice) used in these systems, and 2) additional detector collimation may be used to reduce scatter. The additional collimation may either be a detector slit or a set of fan-beam channels, which in older xenon gas-based detectors were actually part of the detector.

In cone-beam tomography, scatter can be much more severe because the source irradiates a much larger section of the object. Therefore, scatter comes not only from a narrow axial region (or slice) but also from the entire irradiated axial extent. In conventional film radiography, scatter can be reduced by using a variety of scatter rejection grids. These grids are usually comprised of alternating strips of aluminum and lead foil. The strips are focused linearly to the focal spot of the X-ray source and reduce the detection of scattered radiation because, as with the use of collimation for spiral and conventional CT, the ray-path of scatter will typically not come a direction consistent with the X-ray source and will therefore be absorbed by one of the lead strips.

The problems with using these grids for cone-beam tomography is that their transparency—the ratio of the exiting flux to the incident X-ray flux—is relatively low due to both a large number of lead strips (typically 85 or 103 per inch), which must be relatively thick to absorb X-rays of the appropriate energies, and the aluminum used as the interspacer.

Figure 7A:
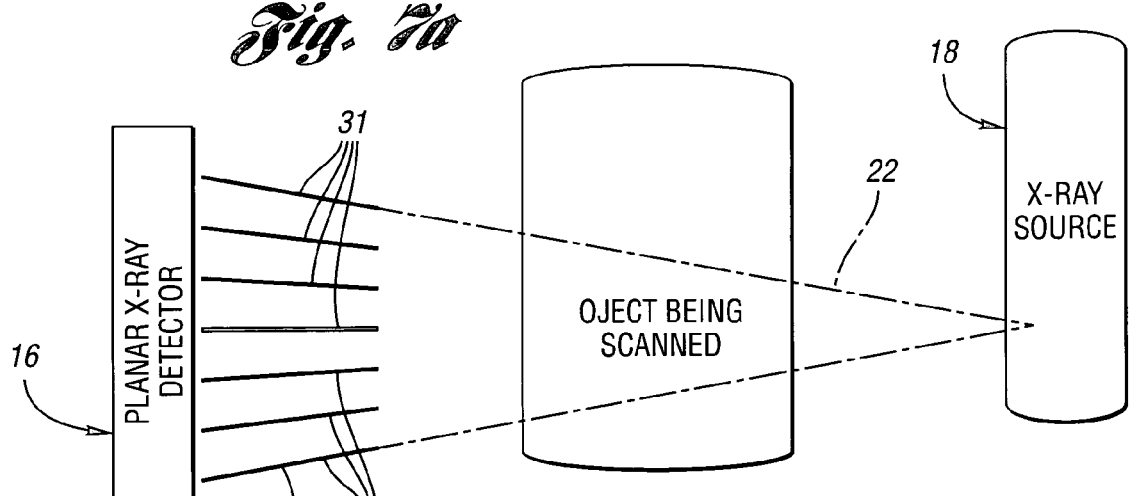
FIGS. 7a and 7b are side and front schematic views, respectively, of a coarse-grained, one-dimensional detector collimator for rejecting X-ray scatter; vanes of the collimator are focused on a focal spot of an X-ray source; an orthogonal set of vanes can be added for improved scatter rejection.
Figure 7B:
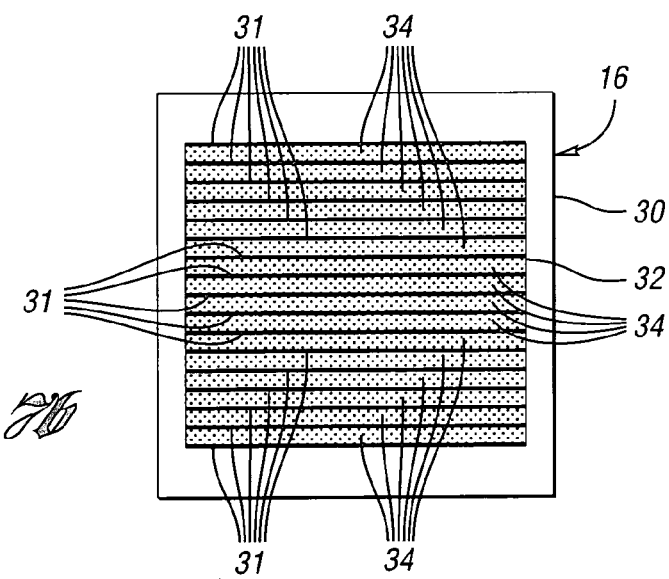

An effective scatter rejection grid with much higher transparency can be constructed with lead foil and machinable polyacrylimide foam—a technique that has been used for constructing slice collimators for SPECT. The basic construction is similar to the conventional grid for radiography described above: each grid or collimator 32 is a stack of absorbing septa 31, focused on the focal-spot of the X-ray source assembly 18, separated by a low-attenuation spacer 34 as shown in FIGS. 7a and 7b. In this case, however, the layers 31 of the scatter rejection grid 32 are much farther apart (perhaps a maximum of 10 foil-foam layers 31 per inch rather than 85). The ratio of the grid, or the ratio of the depth of the linearly focused absorbing septa 31 to the space between septa, can be the same; therefore, the scatter rejection properties can be similar but the transparency much higher (the attenuation of foam is much smaller than aluminum). Two linearly focused grids placed orthogonally with respect to one another can be used to reduce scatter to an even greater degree.

Another method for constructing the crossed grids is to cut slots halfway through each absorbing septum in order to accept corresponding slots cut into orthogonal septa. This results in a largely self-supporting grid (which can be placed within a rigid frame around the perimeter for stability) requiring no foam supports. An additional advantage is that the depth of the grid is reduced by a factor of two.

Yet another technique involves using appropriately corrugated absorbing strips (with corrugations focused on the focal spot of the X-ray source) that are tapered in two dimensions such that the corrugations are focused on the X-ray source. These corrugated septa are then separated by planar septa. This technique is well known in the construction of collimators for nuclear medicine gamma cameras.

Other techniques used in nuclear medicine collimator construction such as casting can also be employed to obtain high-transparency, coarse scatter-rejection grids.

Scatter Reduction Using Source Collimation

The larger the extent of the irradiated portion of the object, the greater the scatter from the object. It is highly desirable from the viewpoints of both reducing patient dose and scattered X-rays that the source only irradiates the necessary portion of the object. In conventional radiography systems this is accomplished by using an adjustable source collimator to restrict the radiation field to the desired region of the object. As noted above, the system described here can use a detector having a width smaller than necessary for acquisition of a complete tomographic dataset. When used in conjunction with a source collimator that only irradiates the portion of the object "seen" by the detector less Compton scatter will be generated (and detected) than in a system using a full-size detector.

As shown in FIGS. 2 and 3 the detector 30, as it moves along its track 35, is connected to the X-ray source collimator 28 through the control arm 24 that ensures that the source 26 only irradiates portions of the object that are visible to the detector 30.

Correction for Residual Scatter

A significant fraction of photons will scatter multiple times within the object and many of these can pass the scatter-rejection grid 32. To reduce the average effect of detected scatter on reconstructed images, it is desirable to employ a method that measures the distribution of residual scatter. Once the mean distribution has been estimated, it can be removed from the data.

The residual detected scatter can be measured by placing a series of beam-stops or shadow masks (i.e., shadow mask 36) between the X-ray source 26 and the object. In the absence of scatter, the shadow of the beam-stops on the detector 30 should record zero photons. Photons that scatter in the object and that pass the scatter rejecting grid 32 will, however, result in some signal in these regions that should have none. If the shadow mask 36 does not perturb the X-ray flux significantly, the signal in these shadow regions can be taken as an estimate of the residual scatter detected at these points. This method has been previously employed for removing scatter from conventional projection radiographs.

In contrast to the aforementioned method, which requires two scans—one with and without the shadow mask 36, or two with the shadow mask 36 in different positions—it is possible to leave the shadow mask 36 in place during the entire scan, which has three desirable consequences. First, the x-ray flux remains unchanged between the scatter measurement and the measurement from which the scatter-free projection is estimated from since they are performed simultaneously. This feature simplifies the correction procedure.

Second, since the shadow mask 36 need not be moved, the overall design is simplified. Finally, since it is not necessary to expose the patient twice to obtain both the diagnostic information and a measure of the scattered radiation, the overall radiation dose to the patient is reduced.

Figure 8:
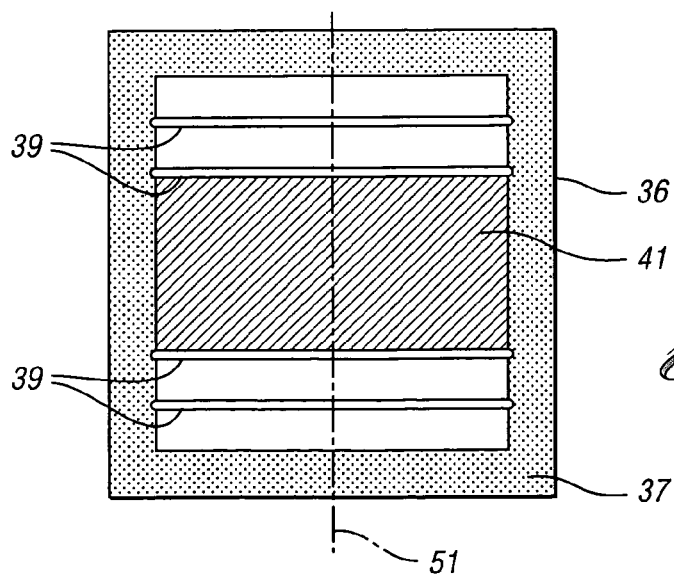
FIG. 8 is a schematic view of a shadow mask that can be used to estimate residual scatter and can be left in place during acquisition of the patient's diagnostic data; additional spatially-variant filtration could be placed within the clear aperture of this mask in order to collect X-ray projection information using two or more X-ray spectra in order to correct for beam hardening and accurately assess bone-mineral content.

There are a number of ways shadow masks can be designed to allow this, one example is shown in FIG. 8. In this case, the absorbing components of the mask 36, such as an absorbing frame 37 and absorbing rods 39, are slightly outside the desired field-of-view 46 (i.e., outside a clear, imaging aperture 41) but since scatter varies smoothly, the detector 30 "sees" approximately the same scatter at these points as it does within the desired region.

Referring to FIGS. 9 through 13, an outline of the procedure for scatter estimation and correction is given as follows:

1. With the shadow mask 36 between the source assembly 18 and the detector assembly 16 and no object in place, a "blank scan" is taken to determine where the shadows of the mask 36 lie on the detector 30.

Figure 9:
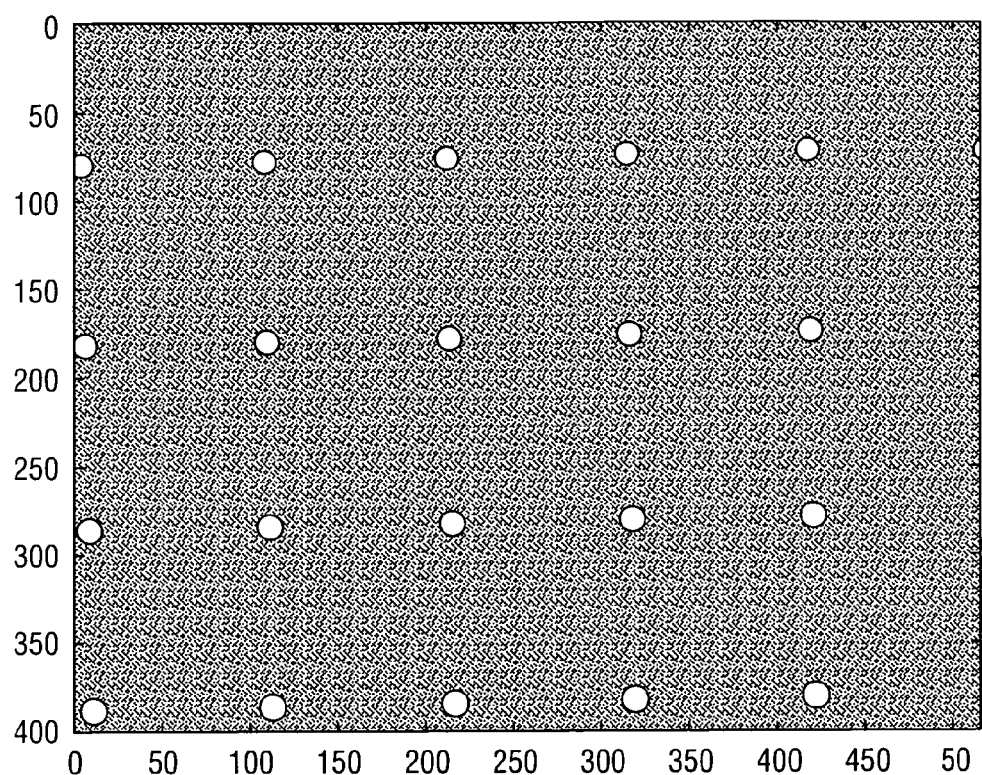
FIG. 9 is a schematic graphical view of a mask for estimating residual scatter computed from a shadow mask consisting of an array of absorbing balls; regions of the mask are slightly smaller than balls.
Figure 10:
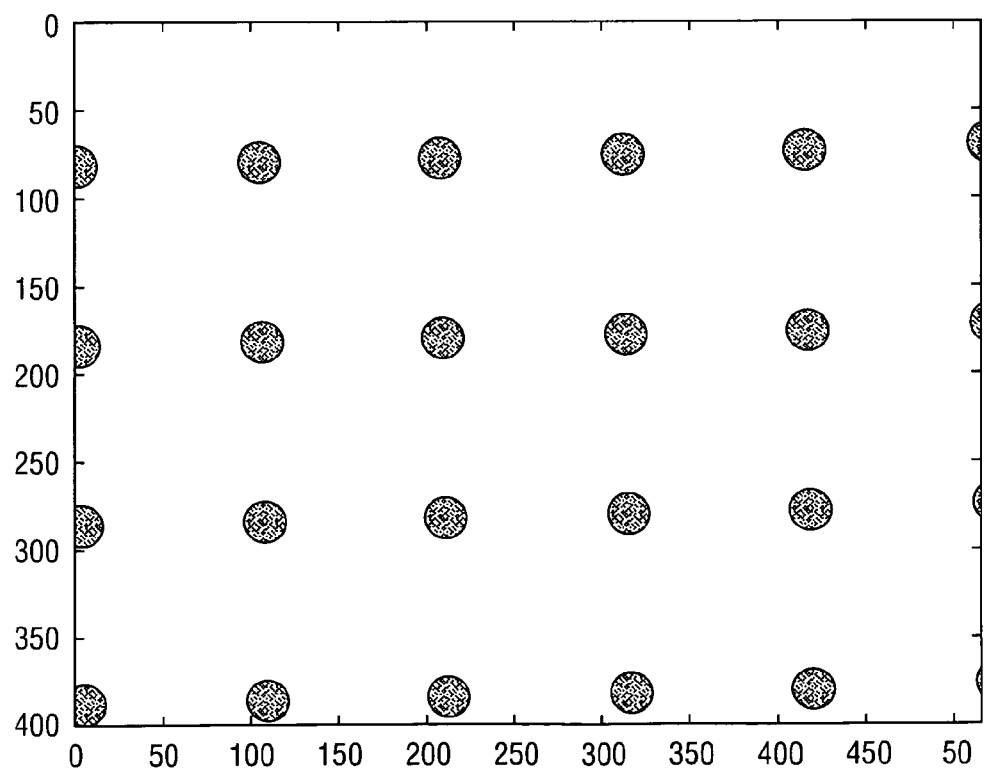
FIG. 10 is a schematic graphical view of a mask for restoring projection data or for use directly in reconstruction algorithms such as penalized weighted least squares (PWLS) so that regions on the detector corresponding to the shadows of the balls are ignored for image reconstruction.

2. This data is then processed to make two digital masks. The first defines regions-of-interest (ROIs) slightly smaller than the actual shadows. These ROIs will be used to estimate the residual scatter (FIG. 9). The second defines regions larger than the shadows (FIG. 10). These regions will be used in the correction process for the diagnostic data (patient scan).

Figure 11:
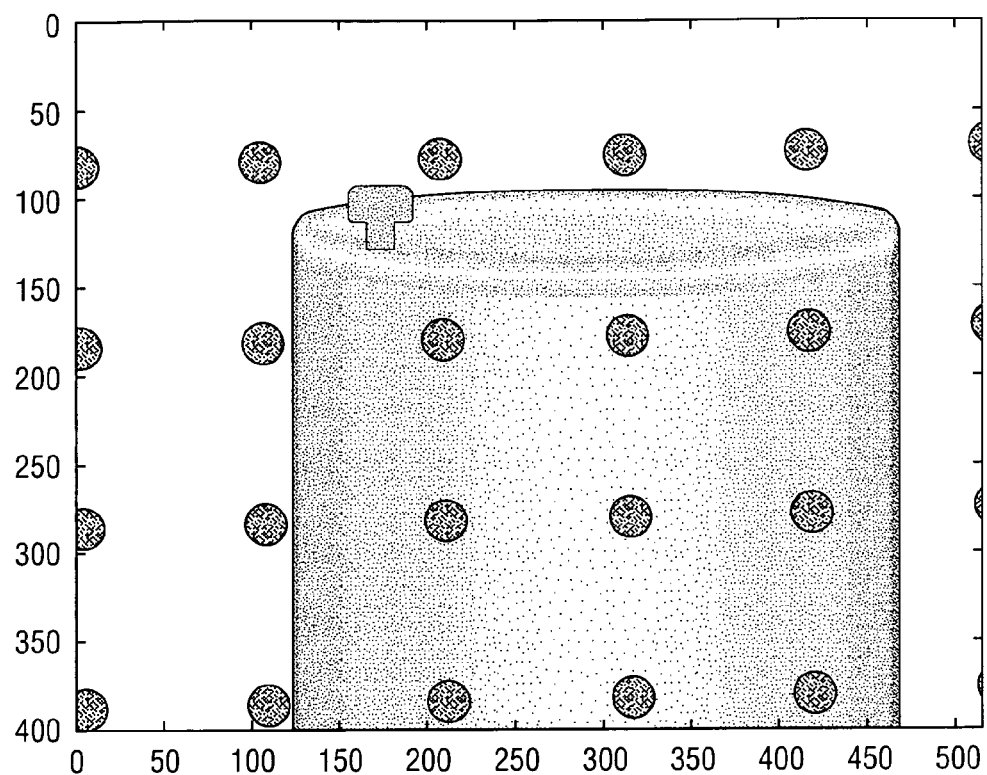
FIG. 11 is a projection image of an object acquired with a ball-array shadow mask interposed between the source and the object.

3. The patient is placed in the tomograph system 10 and scanned with the shadow mask 36 in place (FIG. 11).

4. Using the first mask, the scattered radiation is estimated by the values at each view angle or frame of the patient scan by the values in each frame at every non-zero mask position.

Figure 12:
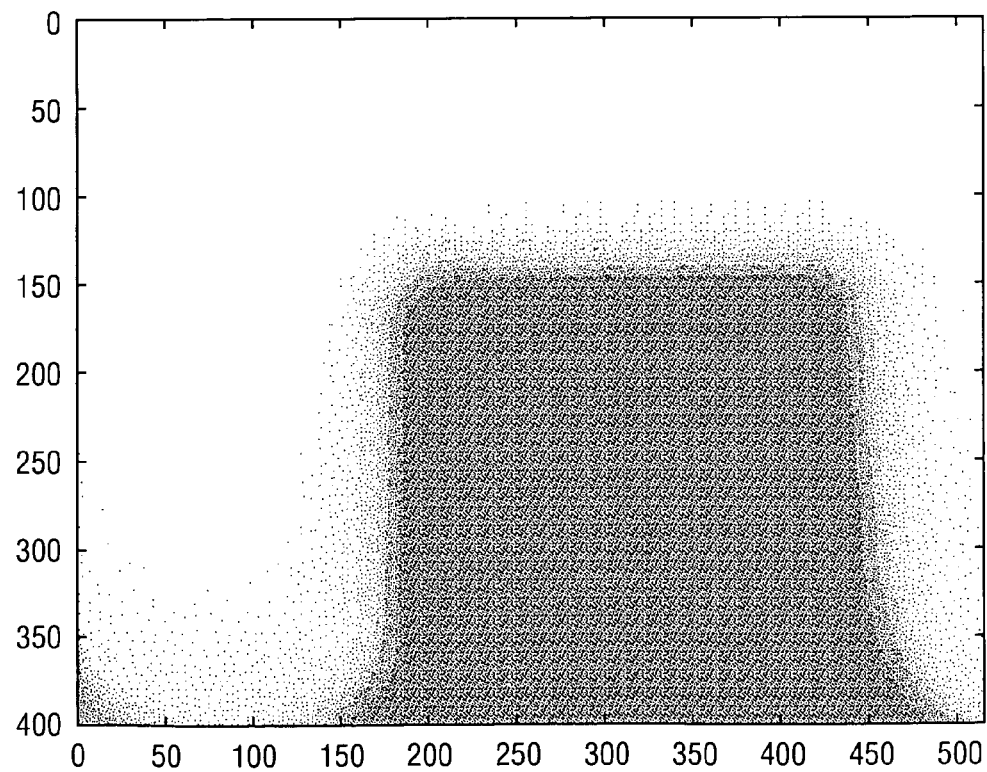
FIG. 12 illustrates spatial distribution of residual scatter estimated using the mask shown in FIG. 9, data shown in FIG. 11, and an appropriate interpolation scheme.
Figure 13:
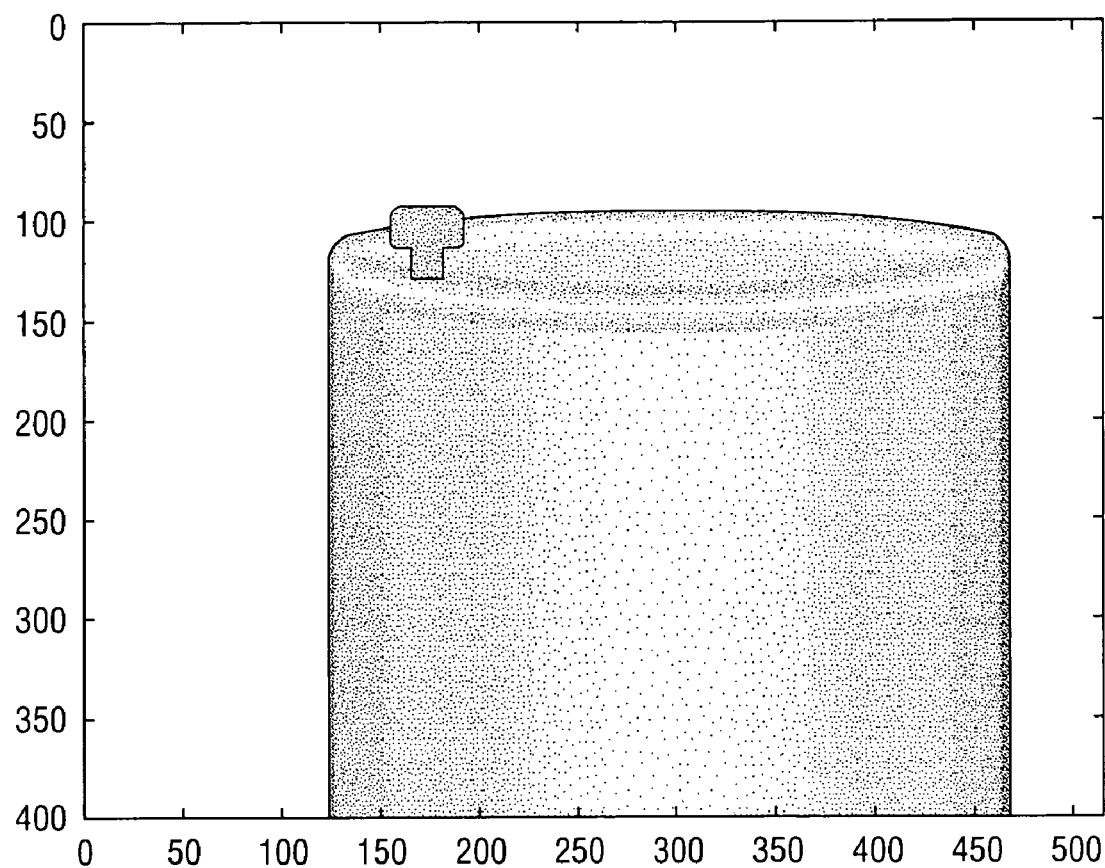
FIG. 13 shows projection data of FIG. 11 that has X-ray scatter removed and has been restored such that the ball array is not evident.
Figure 15A:
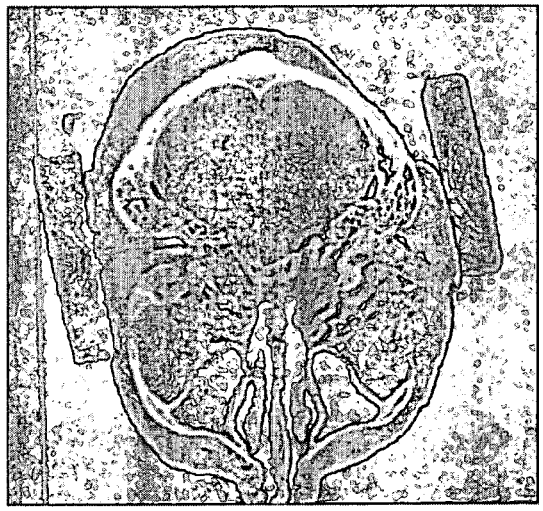
FIGS. 15a-15d illustrate four X-ray CT slices of a human head acquired using prototype tomography for dentomaxillofacial imaging.
Figure 15B:
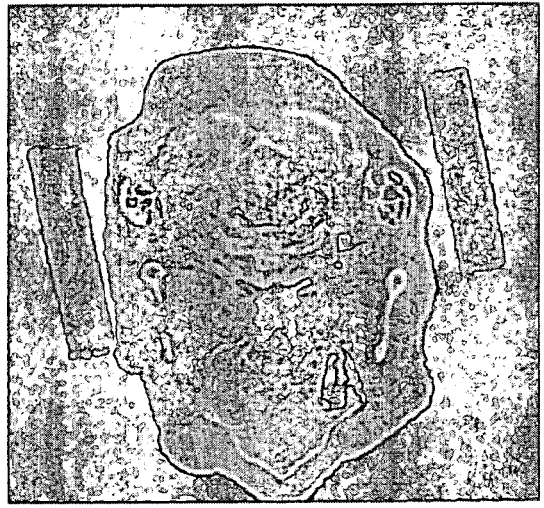
Figure 15C:
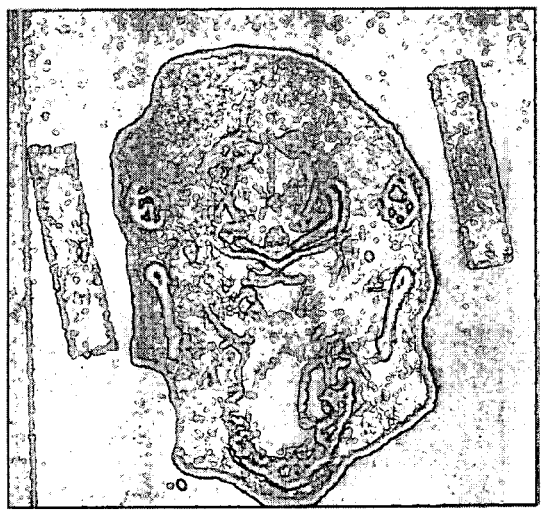
Figure 15D:
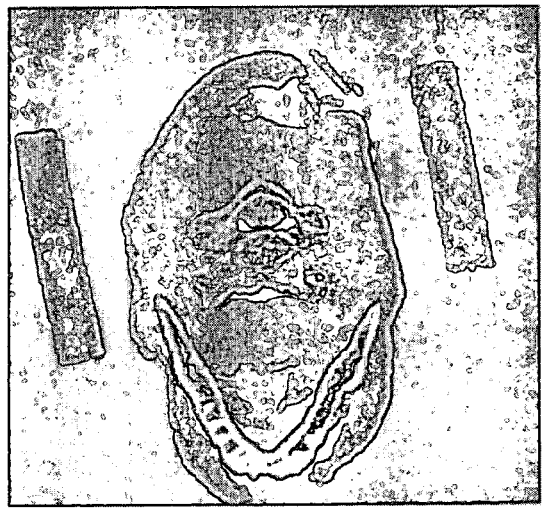

5. The scatter at zero mask positions is then estimated using an interpolation scheme (FIG. 12). A variety of schemes can be used.

6. The scattered information is either explicitly or implicitly (e.g., during the 3D image reconstruction process) subtracted from the patient scan. Using the second mask, information in the shadow regions of the patient scan is "restored" (i.e., as if there were no shadow mask present). The preferred method for restoring this information is to use a penalized, weighted least-squares or penalized maximum likelihood 3D image reconstruction where the mask determines regions of missing data. Alternatively, the information can be estimated on a frame-by-frame basis (shown in FIG. 13), which may, in some cases, be preferable because the amount of computation is significantly reduced.

As noted, there are not only a variety of masks that can be employed but also a variety of estimation/restoration/reconstruction scenarios that can be used.

Moving or "Dithering" Position of Detector to Reduce Effects of Detector Non-Uniformity Detectors always have small spatial non-uniformities of response. Sometimes these can be calibrated out by acquiring a sequence of images with the X-ray source off in order to obtain the "dark signal" or pedestal and another set with the X-ray source on with no object in place ("blank scan") for determining the response or gain of each pixel. Often, however, the signal from a pixel may vary unpredictably when scanning the object. If not taken into account, these signals tend to add coherently in a conventional fan- or cone-beam scanning geometry and will generate rings of higher or lower density in reconstructed images. The magnitude of the ring depends both on the magnitude of the detector defect and its spatial sharpness: sharp-edged defects will generate much larger artifacts than smooth-edged defects.

A way to "smooth" any detector defect is to move the detector 30 along its track 35 a small amount randomly between each frame. This would typically be accomplished by moving the detector 30 under motor control between frames a random—but known—amount corresponding to a maximum of roughly ±20 pixels.

The data acquired in such a fashion are then shifted in the computer 12 after each image frame is collected such that it appears as if the detector 30 as in a single position. Due to the random detector movement, non-uniformities that previously added coherently to produce disturbing visual distortions in the reconstructed images now do not significantly affect reconstructions.

In cone-beam scanning, the more complete orbits described above (i.e., helical and wobbled) further reduce the effect of isolated detector artifacts.

Detector Masking for Pedestal Estimation During Scanning

With the area detector 30, the pedestal or "dark signal" can vary considerably during the scan due to sensitivity of the readout electronics, which are proximal to the detector panel, to small variations in temperature. In ordinary radiography, these pedestal changes present little problem. In computed tomography, however, the changes may be larger than the signal of interest and it is therefore important that they be estimated throughout the scanning interval so that their effects can be removed either during or after the scanning. The varying pedestals in these devices are largely due to the readout amplifiers for each channel. In a device currently in use, each amplifier reads out a column of 256 channels (pixels) with half placed at the bottom edge and the remainder at the top edge of the detector (the detector has an array of 512×512 pixels). If the temperature of the readout chip changes, the offsets are changed for every pixel the amplifier reads out (e.g., an entire column).

Referring now to FIGS. 14a-14c, the detector 30 is shown with gate driver ASICs 61 and readout ASICs 63. In order to estimate pedestals during scanning without acquiring frames when the X-ray source 26 is off (which extends the overall scanning time), portions of the detector 30 adjacent to the integrated circuits containing the readout amplifiers are covered with an X-ray absorbing material 60 (i.e., FIG. 14c). The material 60 covers positions of a scintillator layer 62. Alternatively, the photodiodes on the flat-panel 30 can be masked from light. Although this reduces the active area of the detector 30 slightly, the change in pedestal during the scan for each readout channel can be estimated from the change in the signal observed for the masked channels.

There are numerous methods for estimating the pedestal of each channel from the masked-channel information; the simplest assumes that the change in pedestal for each readout channel is the same for each detector element using a particular readout amplifier (i.e., a row or column of the array depending on orientation) and corrects each digitized detector value by the same digital pedestal change.

An alternative means for accomplishing this without detector masking—assuming the electronics of the detector 30 can be modified—is to have one or several electrical channels on each chip containing readout amplifiers not connected to the array (i.e., everything is similar to active channels but there is no possibility of a signal). These dark channels can then serve as estimates for the change in pedestal for each readout chip during scanning.

Generating Panoramic Images or "Conventional Tomograms" from Reconstructed CT Data Once the 3D volume of attenuation coefficients have been reconstructed from the projection data, the information can be reprojected so that it emulates that acquired using other, more conventional devices such as panoramic X-ray machines or conventional linear tomographs used in dentomaxillofacial imaging. This is useful both for comparing data acquired with the system 10 to previous patient scans and for providing a simple method for "volume rendering" or summarizing the 3D volumetric data in a format familiar to the clinician.

Generating the scans corresponding to those acquired using more conventional devices is summarized by the following procedure:

1. 3D patient data is acquired and reconstructed using the system 10. The result is a volume of linear attenuation coefficients at a particular energy.

2. A linear system model describing how a panoramic X-ray machine or linear tomography generates images from an object is used to map the reconstructed image volume into projections that would have been acquired using a conventional system. This provides the sum of linear attenuation along source-detector paths collected in the conventional instrument.

3. This information is multiplied by −1 and exponentiated to provide the X-ray attenuation the conventional system would have observed. The information can then be displayed digitally or printed on paper or film for presentation.

The key to the above procedure is the system model describing the imaging characteristics (geometry, etc.) for each panoramic system or linear tomography. These linear models can be constructed using methods well known to developers of computed tomography software.

A system constructed in accordance with the present invention may include one or more of the following:

A vertically oriented cone-beam imaging system 10 capable of motions that allow a complete set of tomographic data to be acquired. This is accomplished by not only rotating the gantry 20 but by also allowing it to either pivot on an axis 53 orthogonal to the main rotation axis 51 or by moving the source assembly 18 and detector assembly 16 vertically, parallel to the main axis 51 of rotation during the scan such that the cone-beam completeness conditions are satisfied.

A tomographic system 10 capable of acquiring a complete CT scan with high and isotropic spatial resolution for the dentomaxillofacial complex that additionally is capable of performing both single- and dual-kV ("dual energy") imaging.

The proposed scatter elimination technique using a coarse, high-transparency grid 32 (or crossed coarse grids) as opposed to fine granularity, relatively low-transparency grids.

The shadow mask 36 containing both absorbing elements for scatter estimation and spatially varying filtration for dual-energy imaging for the purpose of correcting beam-hardening artifacts.

The use of a shadow mask 36 that can be left in place during the diagnostic scan and methods for estimating the residual scatter and reconstructing the resulting data.

The use of a low current scout scan to determine the appropriate detector offset in addition to estimating appropriate exposure time (appropriate exposures are presently estimated using a scout scan).

The use of a detector that is smaller than necessary in conjunction with apparatus for moving the detector 30 relative to the source 26 and an appropriate X-ray collimator 28 to improve the precision of measurements by reducing scatter and by measuring some portions of the object twice relative to others.

Adapting the measurement system (X-ray collimation and detector position) dynamically to the size of the object to accomplish the above objectives (i.e., appropriate detector position for each frame is not estimated from scout scan but rather from previous frames).

Estimating the pedestal (or dark signal) for each channel that does not require turning off the X-ray source 26 or acquiring additional "blank" frames between X-ray exposures.

"Dithering" the position of the detector 30 in order to reduce visually disturbing artifacts.

Generating "panoramic" or conventional linear tomography images from the reconstructed CT volume.

Working Models and Simulations

Extensive simulations and a lab-bench prototype model have been constructed and used for imaging phantoms and cadaver heads in order to assess the utility of the system 10 in treatment planning for dental implants. The spatial resolution of the system 10 is approximately 400 microns FWHM in all three spatial dimensions. Moreover, complete data is acquired and both single- and dual-energy scanning have been accomplished. This is in contrast to conventional spiral CT where spatial resolution is closer to 1 mm in the transaxial direction and 1.5-2 mm in the axial direction. Four tomographic slices of a human head are shown in FIGS. 15a-15d.

It is certainly possible to construct a small X-ray CT scanner for imaging the head, neck and extremities in a variety of ways. For example, one can attach a large enough amorphous silicon detector to a rotating gantry and use no additional scatter correction hardware or software and obtain images that may be adequate for planning dental implants in many cases. Nevertheless, when it is desirable to be more quantitative to accurately assess bone quality, for instance, many of the features described above such as dual-energy imaging, scatter correction, and pedestal estimation methods will prove important.

It is also possible to use detectors other than amorphous silicon imaging arrays. For example, image intensifiers and CCD cameras can be and have been used (TomCAT). Nevertheless, simple devices based on these detectors still suffer problems such as scatter, detector size issues, tomographic completeness problems, etc. The methods described above are solutions to those common problems and most do not depend on the type of detector used.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An X-ray computed tomography (CT) system comprising:
    a support structure including a gantry mounted to rotate about a vertical axis of rotation during scanning;
    a first assembly including an X-ray source mounted on the gantry to rotate therewith for generating a cone X-ray beam, wherein the X-ray source is mounted to move a focal spot through a plurality of planes during scanning wherein the plurality of planes are perpendicular to the axis of rotation;
    a second assembly including a planar X-ray detector mounted on the gantry to rotate therewith wherein the detector is spaced from the source on the gantry for enabling a human or other animal body part to be interposed therebetween so as to generate output data comprising a plurality of two-dimensional electronic representations of an area of the detector on which an X-ray beam impinges during scanning;
    and a data processor for processing the output data to obtain a CT image of the body part.

2. A system as claimed in claim 1, wherein the second assembly includes a grid positioned adjacent the detector to reduce scatter.

3. A system as claimed in claim 1, wherein the first assembly includes a shadow mask for spatially modulating the source during scanning and wherein the data processor estimates residual scatter during scanning based upon the spatial modulation by the shadow mask.

4. A system as claimed in claim 1, wherein the data processor is programmed to generate a three-dimensional image of the body part based upon the output data.

5. A system as claimed in claim 1, wherein the first assembly is capable of irradiating the body part with two different X-ray spectra.

6. The system as claimed in claim 1, wherein the first assembly includes a source collimator mounted adjacent the X-ray source.

7. The system as claimed in claim 6 further comprising a device for offsetting the detector in a plane substantially perpendicular to the axis of rotation relative to the gantry, in order to offset the amount of alignment of the detector relative to the X-ray source and the axis of rotation.

8. The system as claimed in claim 7 further comprising an arm coupled to the detector and the source collimator for changing position of the source collimator relative to the source based on position of the detector.

9. The system as claimed in claim 7 further comprising a device for changing a position of the source collimator relative to the source based on a change in position of the detector relative to the source.

10. The system as claimed in claim 1 further comprising a scatter rejection collimator mounted on the gantry to rotate therewith.

11. The system as claimed in claim 1, wherein the detector includes a converter for converting X-ray radiation into visible light.

12. The system as claimed in claim 11, wherein the detector includes a hydrogenated amorphous silicon (aSi:H) detector array.

13. The system as claimed in claim 1, wherein the data processor is programmed to perform a statistical image reconstruction (SIR) on the output data.

14. The system as claimed in claim 1, wherein the data processor is programmed to perform a penalized weighted least squares (PWLS) reconstruction on the output data.

15. The system as claimed in claim 1, wherein the data processor is programmed to perform a dual energy penalized weighted least squares (DL PWLS) reconstruction on the output data.

16. The system as claimed in claim 1, wherein the detector generates high and low energy data at each rotation angle of the gantry during scanning.

17. The system as claimed in claim 16, wherein the data processor is programmed to obtain the high and low energy data from the detector and generate the CT image using the obtained data.

18. The system as claimed in claim 1 further comprising means for correcting for body part motion between a plurality of rotation angles of the gantry wherein the means for correcting includes a device that measures relative motion of the body part to obtain measurement data and wherein the data processor is programmed with an image reconstruction program which utilizes the measurement data.

19. The system as claimed in claim 1, wherein the gantry is also mounted to move vertically along the axis of rotation, and wherein the data processor is programmed to gather the output data while the gantry moves vertically and reconstruct the image of the body part based upon output data gathered during the vertical movement of the gantry relative to the body part.

20. The system as claimed in claim 1, wherein the gantry is also mounted to pivot about an axis not parallel to the axis of rotation.

21. The system as claimed in claim 1 wherein the body part is a head, the system further comprising means for stabilizing motion of the head.

22. The system as claimed in claim 1, wherein the data processor is programmed to generate the CT image at least substantially free from cone-beam artifacts based upon the output data.

23. The system as claimed in claim 1, wherein the data processor is programmed to generate the CT image that at least substantially satisfies Tuy's completeness criteria based upon the output data.

24. The system as claimed in claim 1, wherein at least one of the X-ray source and the X-ray detector is mounted to move in a direction parallel to the axis of rotation during scanning.

25. The system as claimed in claim 24, wherein the X-ray source and the X-ray detector are mounted to perform a helical scan during scanning.

26. An X-ray computed tomography (CT) system comprising:
  a support structure including a gantry mounted to rotate about an axis of rotation;
  a first assembly including an X-ray source mounted on the gantry to rotate therewith for generating a cone X-ray beam;
  a second assembly including an X-ray detector mounted on the gantry to rotate therewith, wherein the detector is spaced from the source on the gantry for enabling a human or other animal body part to be interposed therebetween, the detector generating a two-dimensional electronic representation of an area of the detector on which an X-ray beam impinges at each of a plurality of rotational angles about the axis of rotation during scanning;
  means for measuring a position of the body part at each of the plurality of rotational angles, and
  a data processor for correcting for variation in the position of the body part during scanning between at least two of the plurality of rotational angles, the data processor creating an image of the body part based upon the two-dimensional electronic representations and based upon the correction for variation in the position of the body part between the at least two of the plurality of rotational angles.

27. The system as claimed in claim 26, wherein the data processor is programmed to correct for variation in the position of the body part between a first rotational angle of the plurality of rotational angles and a second rotational angle of the plurality of rotational angles.

28. The system as claimed in claim 27, wherein the data processor is programmed to determine that the body part is at a first position relative to the axis of rotation when the gantry is at the first rotational angle and that the body part is at a second position relative to the axis of rotation when the gantry is at the second rotational angle, the first position different from the second position.

29. An X-ray computed tomography (CT) system comprising:
  a support structure including a gantry mounted to rotate about a vertical axis of rotation;
  a first assembly including an X-ray source mounted on the gantry to rotate therewith for generating a cone X-ray beam, the first assembly further including a shadow mask for spatially modulating the source during scanning;
  a second assembly including a planar X-ray detector mounted on the gantry to rotate therewith wherein the detector is spaced from the source on the gantry for enabling a human or other animal body part to be interposed therebetween so as to be scanned by the X-ray beam to obtain a CT scan and generating output data representative thereof, the output data including a plurality of two-dimensional electronic representations of an area of the detector on which an X-ray beam impinges; and
  a data processor for processing the output data to obtain an image of the body part, the data processor programmed to estimate residual scatter during scanning based upon the spatial modulation by the shadow mask.

30. The system of claim 29, wherein the data processor estimates residual scatter based upon the same output data used to create the image of the body part.

31. The system of claim 30, wherein the data processor estimates residual scatter in one of the plurality of two-dimensional electronic representations based upon the spatial modulation in the one of the two-dimensional electronic representations, wherein the data processor obtains the image of the body part by reconstructing the plurality of two-dimensional electronic representations, including the one of the plurality of two-dimensional electronic representations.

32. The system as claimed in claim 31, wherein the data processor is programmed to use a penalized weighted least squares reconstruction algorithm to restore image information in shadow regions created by the shadow mask.

33. A method for imaging a body part including the steps of:
  a) generating a cone x-ray beam having a focal spot;
  b) directing at least a portion of the cone x-ray beam generally toward a body part from each of a plurality of positions rotationally spaced about an axis;
  c) during said step b), moving the focal spot through a plurality of planes, wherein the plurality of planes are generally perpendicular to the axis; and d) for each of the plurality of positions, storing a two-dimensional representation of the at least a portion of the cone x-ray beam after passing through the body part.

34. The method of claim 33, wherein the cone x-ray beam is generated by an x-ray source, and where said step c) further includes the step of displacing the x-ray source in a dimension parallel to the axis.

35. The method of claim 34, wherein the two-dimensional representations are generated by a detector, and wherein the detector is displaced in the dimension parallel to the axis during said steps a-d).

36. The method of claim 33 further including the step of generating an image of the body part based upon the plurality of two-dimensional representations.

37. An X-ray computed tomography (CT) system comprising:
  a support structure including a gantry mounted to rotate about an axis of rotation during scanning;
  a first assembly including an X-ray source mounted on the gantry to rotate therewith for generating a cone X-ray beam, the first assembly including a source collimator mounted adjacent the X-ray source, wherein the X-ray source is mounted to move a focal spot through a plurality of planes during scanning, wherein the plurality of planes are perpendicular to the axis of rotation;
  a second assembly including a planar X-ray detector mounted on the gantry to rotate therewith wherein the detector is spaced from the source on the gantry for enabling a human or other animal body part to be interposed therebetween so as to generate output data comprising a plurality of two-dimensional electronic representations of the area of the detector on which an X-ray beam impinges during scanning;
  a device for offsetting the detector in a direction substantially perpendicular to the axis of rotation relative to the gantry, in order to offset the amount of alignment of the detector relative to the X-ray source and the axis of rotation;
  an arm coupled to the detector and the source collimator for changing position of the source collimator relative to the source based on position of the detector; and
  and a data processor for processing the output data to obtain a CT image of the body part.

38. A method for imaging a body part including the steps of:
  a) rotating an X-ray source about an axis and about a body part;
  b) generating a two-dimensional electronic representation of an area of the detector on which an X-ray beam impinges at each of a plurality of rotational angles about the axis of rotation during said step of rotating;
  c) determining a position of the body part at each of the plurality of rotational angles; and
  d) correcting for variation in the positions of the body part between at least two of the plurality of rotational angles;
  e) creating an image of the body part based upon the two-dimensional electronic representations and based upon the correction for variation in the position of the body part between the at least two of the plurality of rotational angles.

39. The method as claimed in claim 38, wherein said step d) includes the step of correcting for variation in the position of the body part between a first rotational angle of the plurality of rotational angles and a second rotational angle of the plurality of rotational angles.

40. The method as claimed in claim 39 wherein said step c) further includes the steps of determining that the body part is at a first position relative to the axis of rotation at the first rotational angle and that the body part is at a second position relative to the axis of rotation at the second rotational angle, the first position different from the second position.

41. The method as claimed in claim 39 wherein said step e) is performed after said steps c) and d).

42. The method as claimed in claim 41 wherein the image created in said step e) is a three dimensional image.

* * * * *